(12) United States Patent
Jayaraj

(10) Patent No.: US 9,907,621 B2
(45) Date of Patent: Mar. 6, 2018

(54) SURGICAL PENCIL

(71) Applicant: Prash Jayaraj, Burbank, CA (US)

(72) Inventor: Prash Jayaraj, Burbank, CA (US)

(*) Notice: Subject to any disclaimer, the term of this patent is extended or adjusted under 35 U.S.C. 154(b) by 0 days.

(21) Appl. No.: 14/682,943

(22) Filed: Apr. 9, 2015

(65) Prior Publication Data

US 2015/0216618 A1 Aug. 6, 2015

Related U.S. Application Data

(60) Continuation-in-part of application No. 14/175,907, filed on Feb. 7, 2014, now Pat. No. 9,370,394, which is a division of application No. 13/311,256, filed on Dec. 5, 2011, now Pat. No. 8,690,872, which is a continuation-in-part of application No. 12/615,211, filed on Nov. 9, 2009, now abandoned.

(Continued)

(51) Int. Cl.
| | |
|---|---|
| *A61B 18/14* | (2006.01) |
| *A61B 90/30* | (2016.01) |
| *A61B 1/06* | (2006.01) |
| *A61B 1/00* | (2006.01) |
| *A61B 1/015* | (2006.01) |
| *A61B 90/13* | (2016.01) |
| *A61B 18/00* | (2006.01) |
| *A61B 17/00* | (2006.01) |

(52) U.S. Cl.
CPC .......... *A61B 90/30* (2016.02); *A61B 1/00094* (2013.01); *A61B 1/015* (2013.01); *A61B 1/0607* (2013.01); *A61B 18/1402* (2013.01); *A61B 90/13* (2016.02); *A61B 18/1477* (2013.01); *A61B 2017/00477* (2013.01); *A61B 2018/00601* (2013.01); *A61B 2018/00607* (2013.01); *A61B 2018/00916* (2013.01); *A61B 2018/00946* (2013.01); *A61B 2018/1475* (2013.01); *A61B 2018/1495* (2013.01); *A61B 2090/306* (2016.02); *A61B 2218/008* (2013.01)

(58) Field of Classification Search
CPC .................. A61B 18/1477; A61B 18/1402
See application file for complete search history.

(56) References Cited

U.S. PATENT DOCUMENTS

| | | |
|---|---|---|
| 1,038,011 A | 9/1912 | Snell |
| 2,029,487 A | 2/1936 | Kleine |

(Continued)

FOREIGN PATENT DOCUMENTS

WO 2004/054626 A2 7/2004

OTHER PUBLICATIONS

Valleylab, "Electrosurgical Pencils: A cut above the competition", htpp://www.valleylab.com/product/es/accessories/es_pencils_over.html, Jun. 17, 2009.

(Continued)

*Primary Examiner* — Julianna N Harvey

(74) *Attorney, Agent, or Firm* — K&L Gates LLP; Louis C. Cullman; Brian J. Novak

(57) ABSTRACT

Described herein generally are surgical pencils which define a channel to enable suctioning of materials and methods of operating the surgical pencils. In one example embodiment, the surgical pencils perform cutting and coagulation. In one example embodiment, the surgical pencils include a lighting device.

10 Claims, 21 Drawing Sheets

Related U.S. Application Data

(60) Provisional application No. 61/199,299, filed on Nov. 14, 2008, provisional application No. 61/977,551, filed on Apr. 9, 2014.

(56) References Cited

U.S. PATENT DOCUMENTS

| | | | |
|---|---|---|---|
| 4,688,569 A | 8/1987 | Rabinowitz | |
| 5,181,916 A | 1/1993 | Reynolds et al. | |
| 5,413,575 A | 5/1995 | Haenggi | |
| 5,693,044 A | 12/1997 | Cosmescu | |
| 5,836,944 A | 11/1998 | Cosmescu | |
| 6,210,325 B1 | 4/2001 | Bartie et al. | |
| 6,428,180 B1 | 8/2002 | Karram et al. | |
| 6,558,379 B1 | 5/2003 | Batchelor et al. | |
| 6,562,032 B1 | 5/2003 | Ellman et al. | |
| 7,631,981 B2 | 12/2009 | Miller et al. | |
| 8,690,872 B2 | 4/2014 | Jayaraj | |
| 9,370,394 B2 | 6/2016 | Jayaraj | |
| 2003/0050633 A1 | 3/2003 | Ellman et al. | |
| 2003/0088247 A1 | 5/2003 | Ineson | |
| 2003/0181904 A1* | 9/2003 | Levine | A61B 18/1402 606/45 |
| 2006/0025760 A1 | 2/2006 | Podhajsky | |
| 2006/0095026 A1 | 5/2006 | Ricart et al. | |
| 2007/0027449 A1 | 2/2007 | Godara et al. | |
| 2007/0049927 A1* | 3/2007 | Saltzman | A61B 18/1402 606/45 |
| 2007/0250054 A1 | 10/2007 | Drake | |
| 2009/0062791 A1* | 3/2009 | Lee | A61B 18/1402 606/45 |
| 2010/0087816 A1 | 4/2010 | Roy | |
| 2010/0125172 A1 | 5/2010 | Jayaraj | |

OTHER PUBLICATIONS

U.S. Appl. No. 15/162,286, filed May 23, 2016.

* cited by examiner

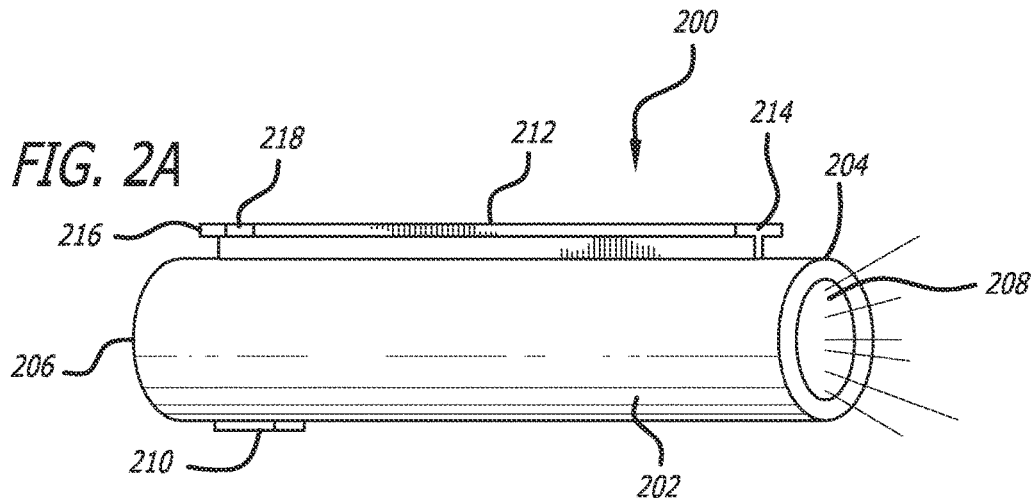
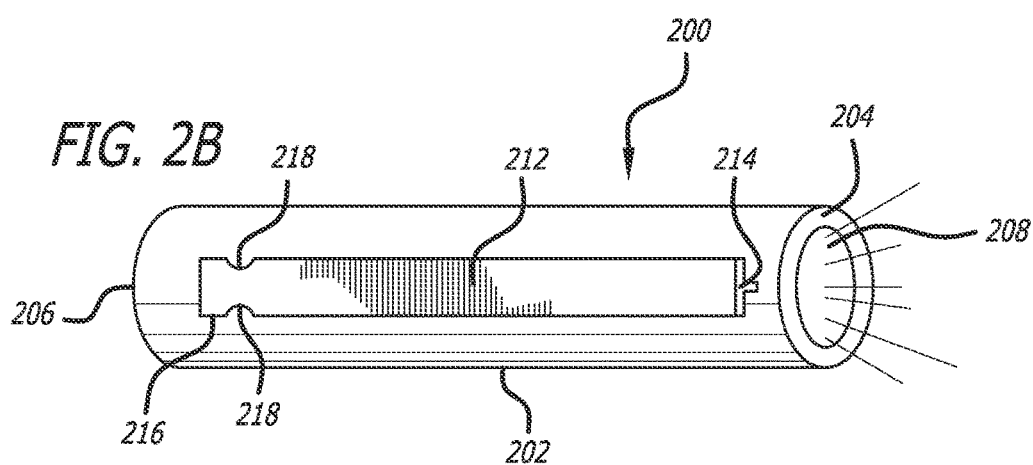
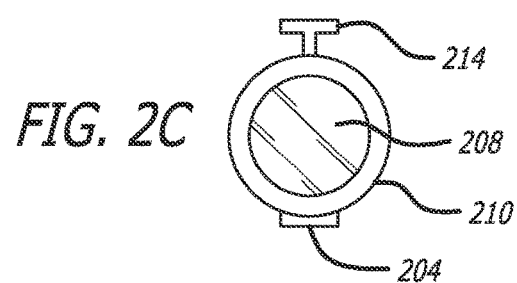

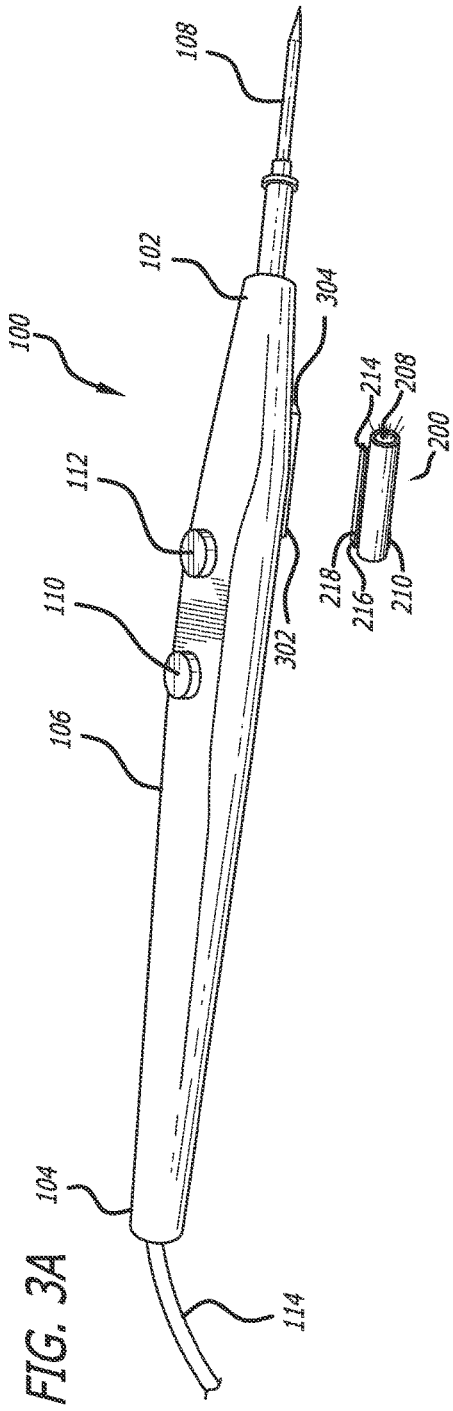
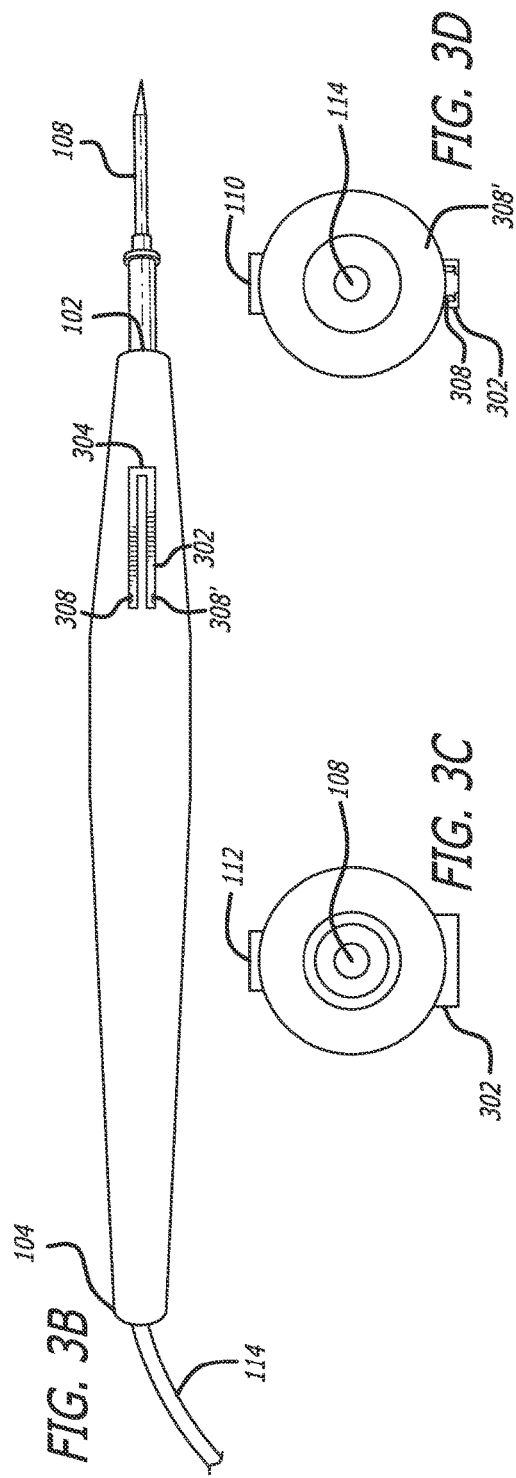

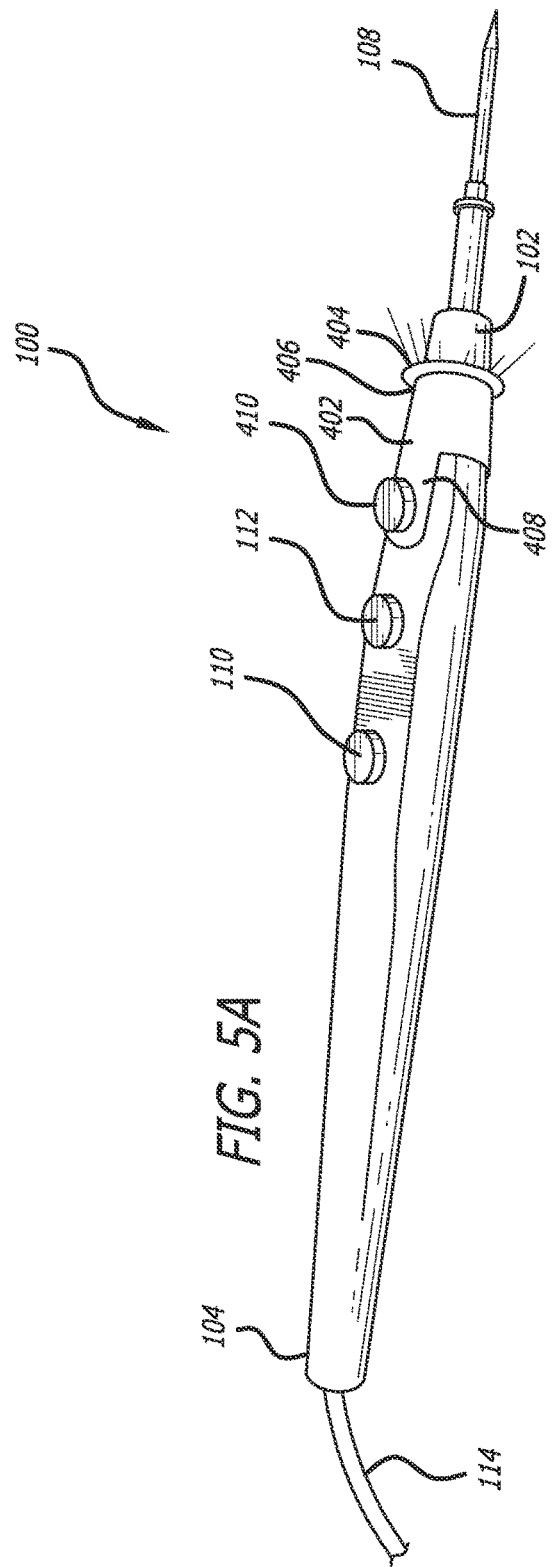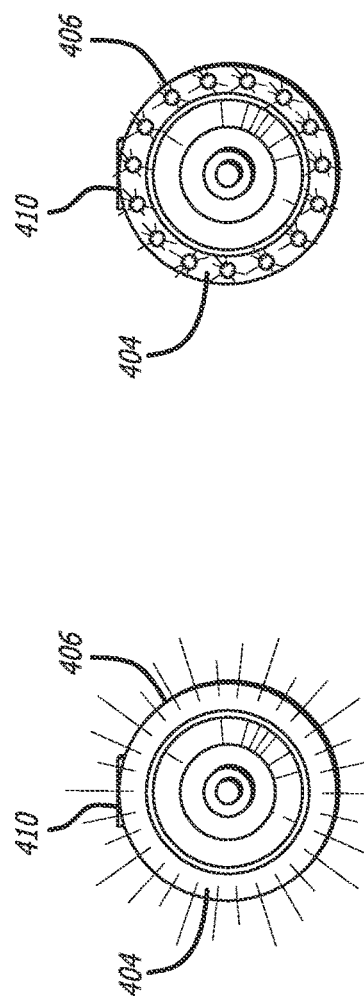

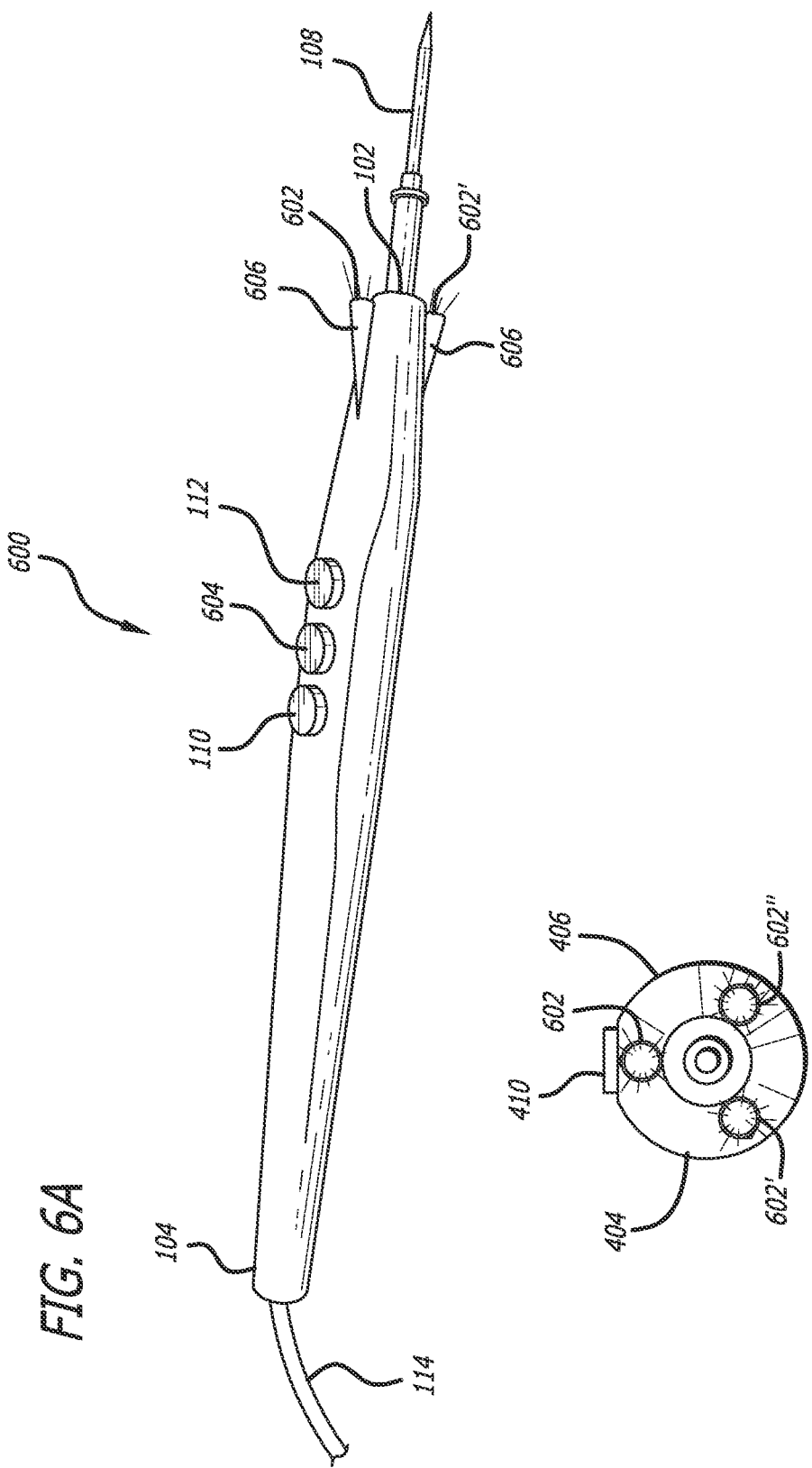

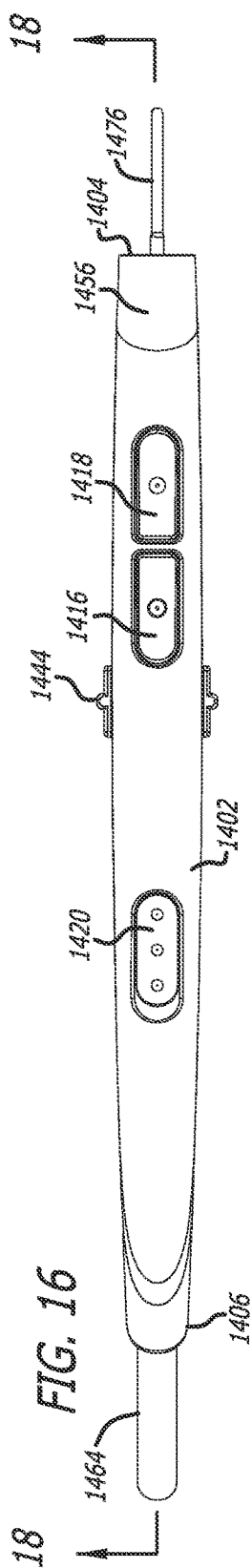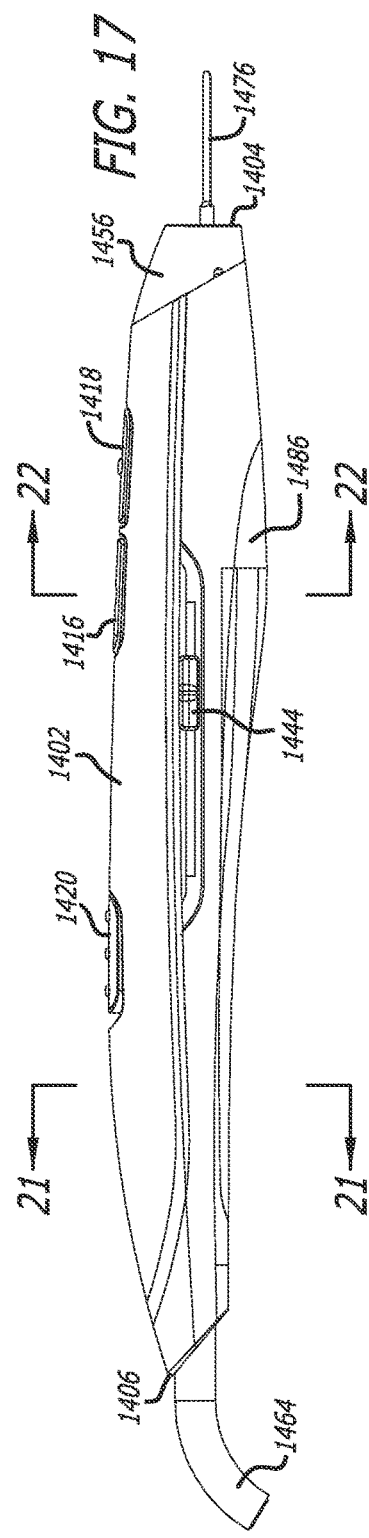

SURGICAL PENCIL

CROSS REFERENCE TO RELATED APPLICATIONS

This application is a continuation-in-part of U.S. patent application Ser. No. 14/175,907, filed Feb. 7, 2014, which is a divisional of U.S. patent application Ser. No. 13/311,256, filed Dec. 5, 2011, now U.S. Pat. No. 8,690,872, which is a continuation-in-part of U.S. patent application Ser. No. 12/615,211, filed Nov. 9, 2009, now abandoned, which claims priority from U.S. Provisional Application Ser. No. 61/199,299, filed Nov. 14, 2008, each of which is incorporated herein by reference in its entirety.

This application claims priority from U.S. Provisional Application Ser. No. 61/977,551, filed Apr. 9, 2014, which is incorporated herein by reference in its entirety.

BACKGROUND

Electrosurgical pencils, or just surgical pencils, have long been used in the medical field for surgical procedures as both a cutting device and a coagulating device. These two uses require two different electric currents with different wave forms. The different electric currents are provided to the electrosurgical pencils generally from an external power source such as an electrosurgical generator. The electrosurgical generator provides electricity in different wave forms and transmits it to the apical end of the electrosurgical pencil that houses a small blade, or other surgical tool, that facilitates the cutting and the coagulating functions. The electricity is transmitted from the tip of the pencil to a ground attached to a patient's body, thereby eliciting the desired function at the small blade attached to the surgical pencil.

The body of a surgical pencil houses a circuit board which is controlled by a switch with appropriate buttons to select and regulate the flow of different electrical wave forms resulting in the desired surgical presentation, e.g. cutting or coagulation. For example, a surgical pencil might have two buttons, one to engage cutting of tissue and the other button for engaging coagulation of tissue. The buttons themselves are either located on the pencil itself in a location that is ergonomic for the surgeon or on foot pedals which the surgeon engages with his/her foot. Both types of button configurations are presently available on the market. Both types of surgical pencils are equally as effective, but their use is dependent on the surgeon's preference.

Typically, surgical procedures using surgical pencils require an additional person at the surgical sight to remove potentially harmful materials such as smoke, blood, tissue or other bodily fluids. Additional people at the surgical sight can increase the cost of the surgical procedure. Further, it may increase the difficulty in performing the surgical procedure due to crowding.

Additionally, despite the success of surgical pencils, there is a need in the art for surgical pencils that have a means for adequately illuminating the surgical site as the tool is being used. Described herein are surgical pencils fulfilling a long felt need in the art.

SUMMARY

Described herein generally are surgical pencils providing a physician with illumination of a surgical site. There is a long felt need in the art for such devices as visualizing of a target surgical site can be burdensome during delicate and otherwise exhausting surgical procedures. The surgical pencils described herein can be retrofitted with a lighting device, can be manufactured incorporating a lighting device or can be fitted with a preformed lighting device.

In one embodiment described herein is a surgical pencil for providing an illuminated surgical site comprising a surgical instrument having a first end, a second end, and elongated structure and a surgical tool associated with the first end; and a removable lighting device associated with the first end of the surgical instrument and operable by a surgeon having a power button, at least one light and a mating mechanism to connect the removable lighting device to the surgical instrument.

In one embodiment, removable lighting device is formed of an elastic polymer or a rigid polymer. In other embodiments, the mating mechanism has a shape that can compliment at least one shape included on the surgical instrument and thereby secure the removable lighting device to the surgical instrument.

In another embodiment, the at least one light is a fiber optic lighting element and/or at least one LED light. The light or lights can be provided in a circular arrangement. The removable lighting device can be powered by a built-in battery and/or be disposable.

In yet another embodiment, the removable lighting device is reusable with the same surgical instrument or a different surgical instrument.

In still other embodiments, the removable lighting device is safe to at least one sterilization technique including, but not limited to gamma irradiation, pressure sterilization and/or steam sterilization.

Further, described herein is a lighting device comprising a power button, at least one light, a housing and a mating mechanism to connect the lighting device to a surgical instrument. In one embodiment, the mating mechanism is an expandable housing formed of an elastic polymer. The polymer can be a rubber if elastic or can be a rigid polymer.

In still further embodiments, the mating mechanism has a shape that can compliment at least one shape included on the surgical instrument and thereby secures the removable lighting device to the surgical instrument.

In some embodiments, the at least one light is a fiber optic lighting element and/or an LED light. The light can be provided in a circular arrangement.

In one embodiment, the surgical pencil defining a channel which enables suction. In one embodiment, the surgical pencil includes a suction device. In one embodiment the surgical pencil is configured to removably connect to a separate suction device.

Additional features and advantages are described herein, and will be apparent from, the following Detailed Description and Figures.

Further, this application incorporates by reference U.S. patent application Ser. No. 13/311,256 filed on Dec. 5, 2011; U.S. patent application Ser. No. 12/615,211 filed on Nov. 9, 2009; and U.S. provisional patent application No. 61/199,299, filed Nov. 14, 2008 in their entirety.

BRIEF DESCRIPTION OF THE DRAWINGS

FIGS. 2A, 2B and 2C illustrate an exemplary lighting device. FIG. 2A is a side view, FIG. 2B is a top view and FIG. 2C is a front view.

FIGS. 3A, 3B, 3C and 3D illustrate the attachment of the exemplary lighting device from FIG. 2 onto a surgical pencil. FIG. 3A is a perspective view, FIG. 3B is a bottom view, FIG. 3C is a front view and FIG. 3D is a back view.

FIG. 4A is a side view, FIG. 4B is a back view, FIG. 4C is a front view and FIG. 4D is a top view.

FIGS. 5A, 5B and 5C illustrate the attachment of the exemplary lighting device from FIG. 4 onto a surgical pencil. FIG. 5A is a perspective view, FIG. 5B is a front view and FIG. 5C is an alternate front view.

FIGS. 6A and 6B illustrate a surgical pencil with at least one lighting device manufactured into the surgical pencil. FIG. 6A is a perspective view and FIG. 6B is a front view.

FIG. 16 illustrates a top view of the surgical pencil in FIG. 14.

FIG. 17 illustrates a side view of the surgical pencil in FIG. 14.

DETAILED DESCRIPTION

The present description generally provides surgical pencils which provide a physician with illumination of at least a portion of a surgical site. There is a long felt need in the art for such a device as visualizing a target surgical site or a portion thereof can be burdensome during a delicate and otherwise exhausting surgical procedure. The surgical pencils described herein can be retrofitted with a lighting device, can be manufactured incorporating a lighting device or can be fitted with a preformed lighting device.

The surgical pencils described herein can also provide suction of materials at a surgical site or during a surgical procedure. Further still, the herein described surgical tools can be configured to be retractable and extendable. In one embodiment, the surgical tool can be retracted or extended to two or more different axial locations and be releasably locked in place. Suction can be uninterrupted by movement of a surgical tool at the surgical site.

Figure 1:
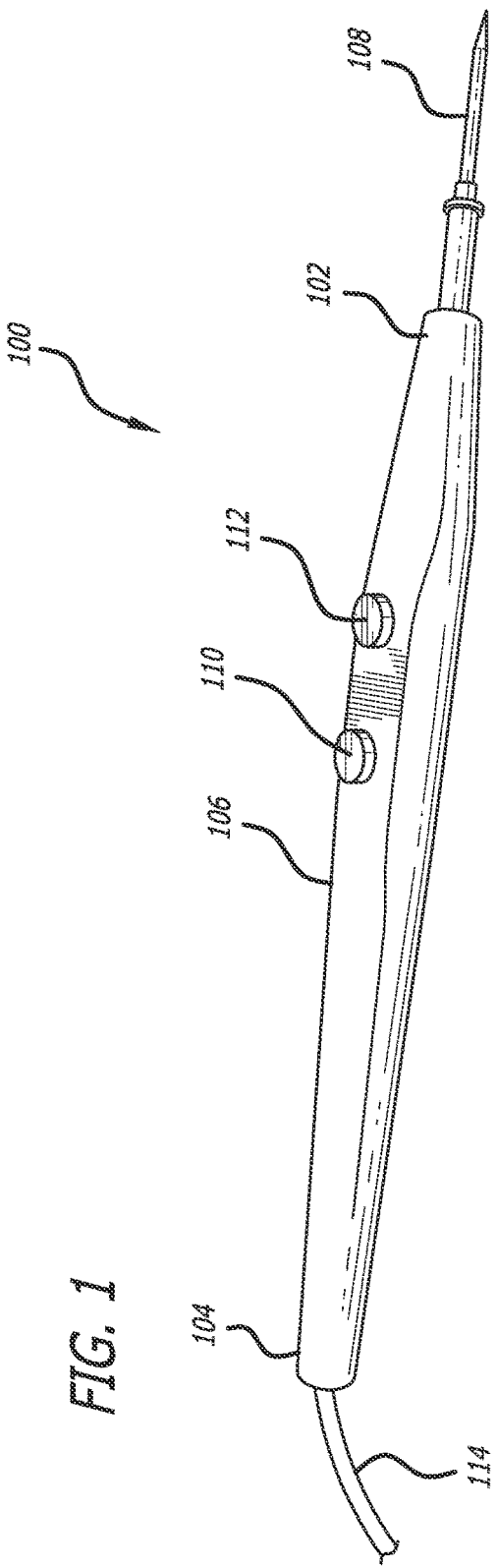
FIG. 1 illustrates a prospective view of a conventional surgical pencil.
Figure 4A:
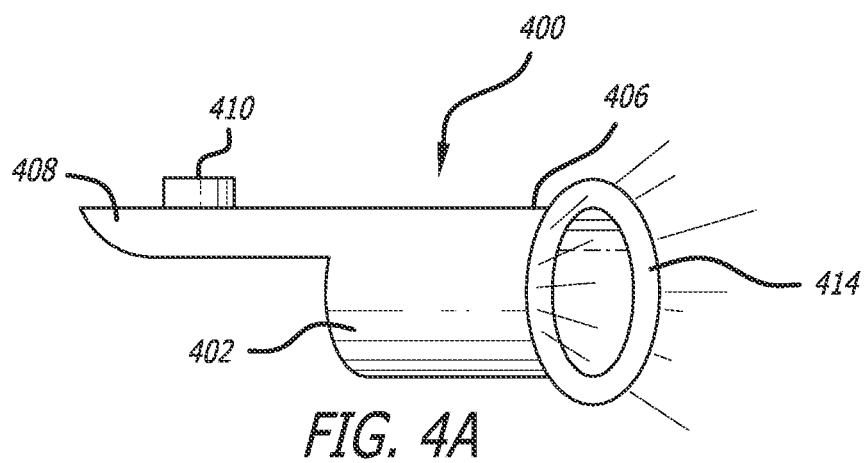
FIGS. 4A, 4B, 4C and 4D illustrate another exemplary lighting device.
Figure 4B:
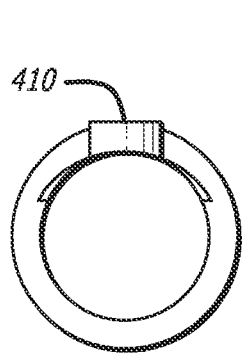
Figure 4C:
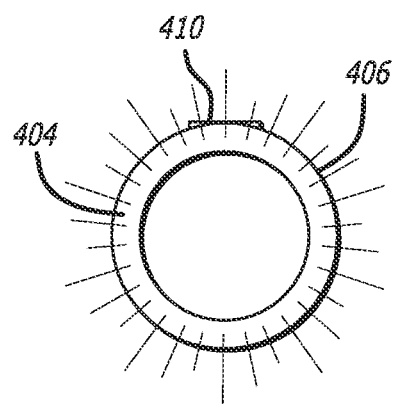
Figure 4D:
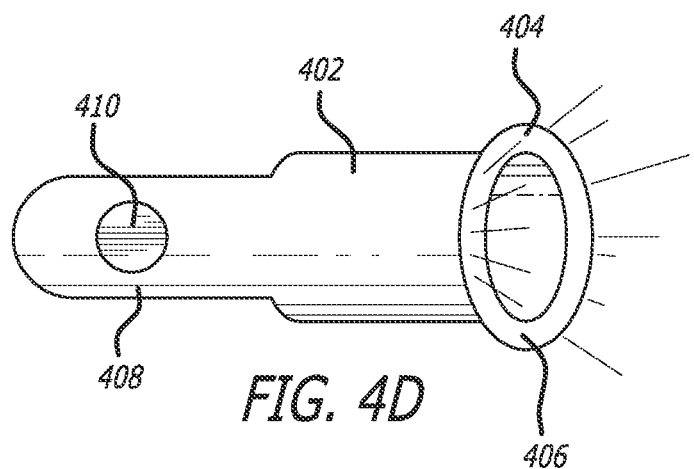

Referring to FIG. 1, a conventional surgical pencil is illustrated. Surgical pencil 100 generally includes first end 102, second end 104, and elongated structure 106 and surgical tool 108 associated with first end 102. Surgical tool 108 can take many forms which are known in the art, but an exemplary tool is a metal tip that is used to seal cuts during surgery. Surgical pencil 100 further includes first button 110 and second button 112 each independently used to cut and cauterize during surgery. In one embodiment, first button 110 can be used to cauterize and second button 112 can be used to cut. The opposite configuration is also possible. Surgical pen 100 also includes cable 114 which provides power to the device's surgical tool 108. Alternatively, surgical pencil 100 can include an independent power supply such as a self contained motor or battery.

Surgical pencil 100 can be contoured to fit comfortably within a physicians hand during surgery. For example elongated structure 106 can have one or more contours, for example, slope 116 for resting and gripping with one or more fingers. Further, first button 110 and second button 112 are located on elongated structure 106 at places that are easily accessed with one or more fingers during surgery without loss of dexterity and accuracy of surgical pencil 100.

The devices described herein further provide surgical pencil 100 with a lighting device used to illuminate the surgical site for which surgical pencil 100 is being used. The lighting device can be independently powered, for example by an internal battery, or can be powered externally, for example, by the pencil itself. Even further still, the lighting device can be retrofitted onto surgical pencil 100, can be manufactured into surgical pencil 100 or can be fitted onto a proprietary surgical pencil.

One example of a lighting device described herein is illustrated in FIGS. 2 A-C. Lighting device 200 has substantially cylindrical body 202 with first end 204 and second end 206. The shape of lighting device 200 can be any shape conceivable in the art, for example, rectangular, triangular, or the like. At least one light 208 is located on first end 204 and projects light waves therefrom.

Lighting device 200 has at least one button 210 for controlling light 208. Button 210 can be any style button that controls the functions of light 208. For example, a push button can be used to turn light 208 on and off. Alternatively, a twisting button can be used to further control the intensity or focus of light 208. In one example embodiment, a single button can incorporate both the functions of a push button and twist button.

Lighting device 200 further includes at least one attachment mechanism to couple lighting device 200 to surgical pencil 100. In one example embodiment, the attachment mechanism is slide rail 212 having a leading end 214 and a trailing end 216. Slide rail can further include at least one locking mechanism, for example, indentations 218, 218' to hold lighting device 200 onto surgical pencil 100.

FIGS. 3 A-D illustrate the accompanying mechanism located on surgical pencil 100. Surgical pencil 100 includes mating mechanism 302 to engage slide rail 212 located on the lighting device 200. Mating mechanism 302 can be located, for example, on the bottom of surgical pencil 100. In other embodiments, mating mechanism 302 can be located on the side of surgical pencil 100 or on the top. The location of mating device 302 is dependent on the needs and comfort of the operating surgeon. Slide rail 212 can slide within mating mechanism 302 until leading end 214 abuts stopping point 304. Mating mechanism 302 includes at least two rails 306 on top of which slide rail 212 can advance until stopping point 304. Mating mechanism can further include at least one locking mechanism, for example, protrusions 308, 308' to hold slide rail 212 within mating mechanism 302.

Alternatively, mating mechanism can be progressively narrower as slide rail 212 is advanced to stopping point 304. Such an approach will allow friction to hold lighting device 200 on surgical pencil 100. Other methods of mating lighting devices to surgical pencils can be used, for example, snaps, VELCRO®, glue, bands, locking rings, and the like. However, whichever method is used, lighting device 200 should be secured to surgical pencil 100 in such a manner as to not allow disconnection during a surgical procedure.

Another example lighting device is illustrated in FIGS. 4 A-D. Lighting device 400 includes expandable body 402 which is generally circular. At least one light 404 is located on front end 406 on projects light waves therefrom. In one example embodiment, light 404 is a circular light that completely spans the circumference of front end 406.

Lighting device 400 further includes control flap 408 which includes at least one button 410. Button 410 can be any style button that controls the functions of light 404. For example, a push button can be used to turn light 404 on and off. Or, a twisting button can be used to further control the intensity or focus of light 404. Button 410 can be of a similar style to buttons found on a surgical pencil. In one example embodiment, a single button can incorporate both the functions of a push button and twist button.

In one example embodiment, lighting device 400 can be formed into the shape of a finger grip. Even further, on some embodiments, a surgeon can instantly custom mold their particular grip into a lighting device or the lighting device can be manufactured having a particular finger grip configuration. Manipulatable hydrogels and other polymers can be used to instantly conform the lighting device to a particular finger grip configuration. Such hydrogels are commonly referred to as "memory gels" in the polymer arts. Further, the lighting device can be configured for right and left hand gripping.

FIGS. 5 A-C illustrate how lighting device 400 is mated with surgical pen 100. Lighting device 400 is made of an expandable material, therefore, before being installed on a surgical pencil, the diameter of expandable body 402 is preferably smaller than the diameter of the surgical pencil. Lighting device 400 is pulled over first end 102 of surgical pencil 100 until it is snug. Expendable body 402 of lighting device 400 allows friction to provide a snug fit around surgical pencil 100.

In one example embodiment, the lighting device 400 is installed onto surgical pencil 100 in such a location that button 410 is situated as a third button on the top of surgical pencil 100. This location for button 410 allows a surgeon easy access to the functions and features not only of the surgical pencil itself, but also the attached light.

Yet another example lighting device is illustrated in FIGS. 6 A-B. Lighted surgical pencil 600 is a modified version of surgical pencil 100 illustrated in FIG. 1 that has at least one light 602 manufactured into or as part of a surgical pencil. Surgical pencil 600 has at least one additional button 604 for controlling at least one light 602. Additional button 604 is located adjacent to first button 110 and second button 112 for ease of use and can be any style button that controls the functions of at least one light 602. For example, a push button can be used to turn at least one light 602 on and off. Or, a twisting button can be used to further control the intensity or focus of at least one light 602.

In FIGS. 6 A and B, at least one light 602 is located within housing 606. Housing 606 is preferably manufactured from similar materials as the surgical pencil itself and is meant to be streamlined so as to not interfere with the use of and grip onto the surgical pencil.

The light used with any device described herein can be any light that provides sufficient light to adequately illuminate a surgical site. Exemplary lights include fluorescent lights, light emitting diodes (LEDs), xenon lights, fiber optic lights (e.g. light guides) and the like. For example, in one embodiment, lighting device 400 can include a fiber optic light that is situated in a circle spanning the diameter of front end 406 thereof. In another embodiment, multiple LEDs can be situated in a circular pattern around the same circumference.

The selection of light can be dependent on the type of lighting device used and the particular surgery. For example, in a disposable lighting device, a lower cost LED light or lights can be ideal. However, in a higher cost reusable precision lighting device, a xenon light or fiber optic light can be ideal.

The lights and lighting devices described herein and used with any device described herein are generally powered by one or more batteries. However, the lighting devices or lights themselves can be powered by the current running through the surgical pencil. For example, an illuminated surgical pencil can have at least one light that is powered by the current running through the pencil. If one or more batteries are used, they should be small enough to fit within the body of a lighting device.

The lighting devices themselves have bodies or casings made of non-conductive materials such as polymers. Exemplary polymers include, but are not limited to polyurethanes, silicones, polyesters such as polyolefins, polyisobutylene and ethylene-alphaolefin copolymers; acrylic polymers and copolymers, ethylene-co-vinylacetate, polybutylmethacrylate, vinyl halide polymers and copolymers, such as polyvinyl chloride; polyvinyl ethers, such as polyvinyl methyl ether; polyvinylidene halides, such as polyvinylidene fluoride and polyvinylidene chloride; polyacrylonitrile, polyvinyl ketones; polyvinyl aromatics, such as polystyrene, polyvinyl esters, such as polyvinyl acetate; copolymers of vinyl monomers with each other and olefins, such as ethylene-methyl methacrylate copolymers, acrylonitrile-styrene copolymers, ABS resins, and ethylene-vinyl acetate copolymers; polyamides, such as Nylon 66 and polycaprolactam; alkyd resins; polycarbonates; polyoxymethylenes; polyimides; polyethers; epoxy resins, polyurethanes; rayon; rayon-triacetate; cellulose, cellulose acetate, cellulose butyrate; cellulose acetate butyrate; cellophane; cellulose nitrate; cellulose propionate; cellulose ethers; carboxymethyl cellulose; synthetic and natural rubbers such as polysiloxanes, latex, polymerized isoprene, bromo isobutylene isoprene, chloro isobutylene isoprene, polychloroprene, chlorosulphonated polyethylene, ethylene propylene, ethylene propylene diene monomer, fluoro silicone, hydrogenated nitrile butadiene, polyisoprene, isobutylene isoprene butyl, methyl vinyl silicone, acrylonitrile butadiene, acrylonitrile butadiene carboxy monomer, styrene butadiene, epichlorodydrin; and combinations thereof.

The polymer or combination of polymers chosen to form the bodies or casings of the lighting devices must be rigid enough to hold a particular configuration and perform its intended function. In some example embodiments, the polymer used is a thermal set rigid plastic. In other embodiments, the polymer is a flexible nylon or rubber polymer. For example, a lighting device as illustrated in FIGS. 4 and 5 can be formed of a flexible rubber or nylon polymer that has a shape memory that can stretch and return to its original un-stretched form after use.

One or more lens is used in conjunction with the lighting devices described herein to focus the light onto the surgical tissue or tissues of interest. The lenses can be made of plastics or glass or may be formed of a transparent polymer used to make the housing. The lenses can be made to provide a particular local length to the light. For example, curvature of the inner or outer surface of the lens, thickness of the lens, refractive index of the lens and the like can be used to provide a particular focal length. An exemplary focal length of the light is generally from the lens to the tip of the cutting device. Such a focal length can be adjusted, however, using a button or a dial to move the lens closer or farther from the light. An exemplary focal length is about 3.0 cm, or about 4.0 cm or about 5.0 cm. In one exemplary embodiment, the focal length is about 4.5 cm.

The lighting devices, in one embodiment, can be reusable. In such a case, the lighting devices are washable and sterilizable using conventional sterilization techniques. For example, the lighting devices must be sealed sufficiently to allow multiple washings with a detergent or alcohol based cleaner without damaging the device. Further, for example, the devices can be sterilized using gamma irradiation techniques.

In other example embodiments, the lighting devices are disposable. Such single use devices are generally used for a single surgical procedure and then discarded in an appropriate manner consistent with health regulations. Even if a lighting device is disposable, the surgical pencil used does not have to be disposable. For example, a non-disposable surgical pencil can be used with many disposable lighting devices.

The lighting devices described herein generally emit light in the visible range to aid a surgeon in a surgical procedure by illuminating the target surgical site. However, in addition to illuminating the target surgical site, the lighting devices can further include a laser light source to provide guidance to a surgeon by providing a line indicating where the incision is likely to end up. Such a laser light can indicate to a surgeon where exactly a cut using the surgical pencil is likely to proceed. This laser light source can be useful in avoiding delicate tissues.

Other specific visible wavelengths of light can be used. For example, if fluorescent surgical markings are used to indicate cuts to be made on a target tissue, a conventional "black light" can be used in the lighting devices described herein to highlight the surgical markings.

Even further still, in some embodiments, the lighting devices can include a microchip that wirelessly communicates with virtual surgical devices. For example, virtual surgery techniques provide computer generated surgical markings which can be followed by a surgeon on one or more displays. With a microchip as described, virtual surgical device systems can track the location of the surgical pen relative to the surgical markings and depict that location on a screen with one or more virtual markings. Such an embodiment can aid a surgeon for example in a microsurgery.

The microchip can also be associated with a gyroscope. The gyroscope can provide the microchip with information about the surgical pencil's orientation. Based on this information, the microchip can control the focus and direction of light emitted from a lighting device. For example, lighting device 200 can include a microchip and gyroscope. In such an embodiment, light 208 can be directed by a microchip. So, if a surgeon moves the pencil in a particular direction, the gyroscope detects that change in direction, the microchip translates that directional change and the direction and focus of at least one light is changed to accommodate for this directional change. This gyroscopic system can aid a surgeon by keeping the light focused and steady despite small changes in angular movement by the surgeon's hand. In other words, the light remains stabilized despite small movements of the hand.

The lighting devices and illuminated surgical pencil devices described herein provide specific advantages for patient and physician comfort as well as to a surgeon's stamina by illuminating the surgical site locally from the surgical pencil itself. One advantage, if desired, is allowing the surgery to take place under ambient or low ambient light conditions without sacrificing complete and accurate visualization of a target surgical field or a portion thereof. These capacities can be ideal for a surgeon and surgical team used to working long hours under bright lights that generate intense heat in order to visualize the target surgical area and that can result in previously unavoidable surgeon discomfort and fatigue. Additionally, it is not uncommon for a surgeon to be wearing several layers of clothing along with surgical barriers, including gloves, face barriers, goggles, hats, and overcoats, to name a few, during a given surgical procedure, further contributing to the discomfort and fatigue normally associated with hot and bright surgical working environments.

Compounding matters, the complexity of contemporary operating rooms has increased over the years as a result of the extra equipment, fixtures, associated power cords and the like required for ever more complicated surgeries. Such situations are not conducive to comfortable, non-fatiguing surgical environments. The ease of use and ambient lighting requirements of the presently described lighting devices and illuminated surgical pencil devices can address and overcome these issues.

Further, the illuminated surgical pencils described herein can provide illumination to the surgical site thereby alleviating the need for a surgeon or other user to wear cumbersome headlamps or other lighting or visualization devices. Such cumbersome devices can cause fatigue. The presently described surgical pencils can reduce fatigue resulting from cumbersome headlamps or other lighting or visualization devices.

As an additional benefit directly from the present lighting devices and illuminated surgical pencil devices, the ambient or low ambient lighting conditions that now can be utilized without sacrificing visualization and control also reduce reflected glare and high contrast shadows in the surgical environment that, in the past, could confuse or possibly even overwhelm the vision of the surgeon. Previously, a related visual limitation in surgery was that a surgeon commonly required surgical team members or students to position themselves out of certain areas in order to reduce shadows that they might cast on the target surgical site. This resulted in limiting their view of the surgery. The present lighting devices addresses this problem by reducing shadows and increasing visibility, especially of the target site by providing light directly to the surgical site from the surgical pencil itself.

Similarly, it is not uncommon for a surgeon to look away from a target surgical site in order to change or to move equipment, to take a mental break, or to communicate with a surgical team or students. Upon looking back onto the traditional target surgical site, the surgeon would have to wait briefly to allow his eyes to adjust to the high intensity lighting, causing delays in the procedure. The present lighting devices and illuminated surgical pencil devices eliminate this problem under normal or low ambient light conditions while still providing effective surgical reference indicia.

Even further still, the use of the present lighting devices and illuminated surgical pencil devices allows a surgical team to position themselves in the most appropriate location for the surgery, not necessarily where the high intensity light and resulting shadows dictate. Moreover, the present lighting devices and illuminated surgical pencil devices provide an ideal environment for students to observe a procedure in comfortable ambient to low ambient light conditions without the associated fatigue.

The use of ambient or low ambient light in medical or surgical processes and the resulting reduced heat and complexity in the operating room also adds to the comfort of a surgical patient and enhances the compliance of the patient with the needs of the surgeon. Patient comfort during a surgical procedure is very important, especially when the patient is under local anesthesia and is conscious. It is not uncommon for bright lights to be focused on at least a portion of a patient, typically on the target surgical site. Such lighting systems can get hot and make a patient uncomfortable. Patients who are uncomfortable commonly are more on edge, squirm and/or twitch, or are tense. These are not ideal situations for a patient undergoing surgery. The present lighting device's ability to adequately illuminate a surgical site without the need to direct high intensity lighting during use can simplify and shorten a medical procedure, provide enhanced patient comfort and compliance, and improve the medical procedure's outcome; all while providing the surgeon with enhanced visual control of the process.

In one example embodiment, the surgical pencil includes or defines a channel or passage which enables suctioning and discharging of materials (e.g., smoke, blood, tissue, and/or other bodily fluids). In some embodiments, the surgical pencil includes a suction device that is separate from the surgical pencil. In other embodiments, the surgical pencil includes the suction device. That is, the suction device is entirely integrated within the surgical pencil.

In the general operation of one embodiment, during a surgical procedure, the surgical pencil can enable a user to (a) operate the surgical pencil as a cutting device; (b) operate the surgical pencil as a coagulation device; and (c) suction materials (e.g., smoke, blood, tissue and/or other bodily fluids) at the point of surgery. The user is also enabled to cause the surgical pencil to operate in an extended state or a retracted state. In one example embodiment, where the surgical pencil has an extended state, a surgical tool (e.g., a metal tip) is extended such that the metal tip may be used to seal a cut during surgery. In one example embodiment, where the surgical pencil has a retracted state, the surgical tool is retracted such that the surgical tool is housed or enclosed by a component of the surgical pencil. In this example, with the surgical tool being in a retracted state, the user is enabled to position an end of the suctioning channel closer to the point of surgery to provide for a more effective suction of materials.

In one example embodiment, whether or not the surgical pencil is suctioning is independent of the surgical pencil's operating state (i.e., the extended or the retracted). That is, the surgical pencil operates to suction materials regardless of the current operating state of the surgical pencil.

As mentioned above, certain surgical procedures relating to cutting and coagulation require the controlled suction and removal of materials such as smoke and blood. Using the surgical pencils and methods disclosed herein, the need for a dedicated person at the surgical site to remove smoke and/or blood is eliminated.

Figure 10A:
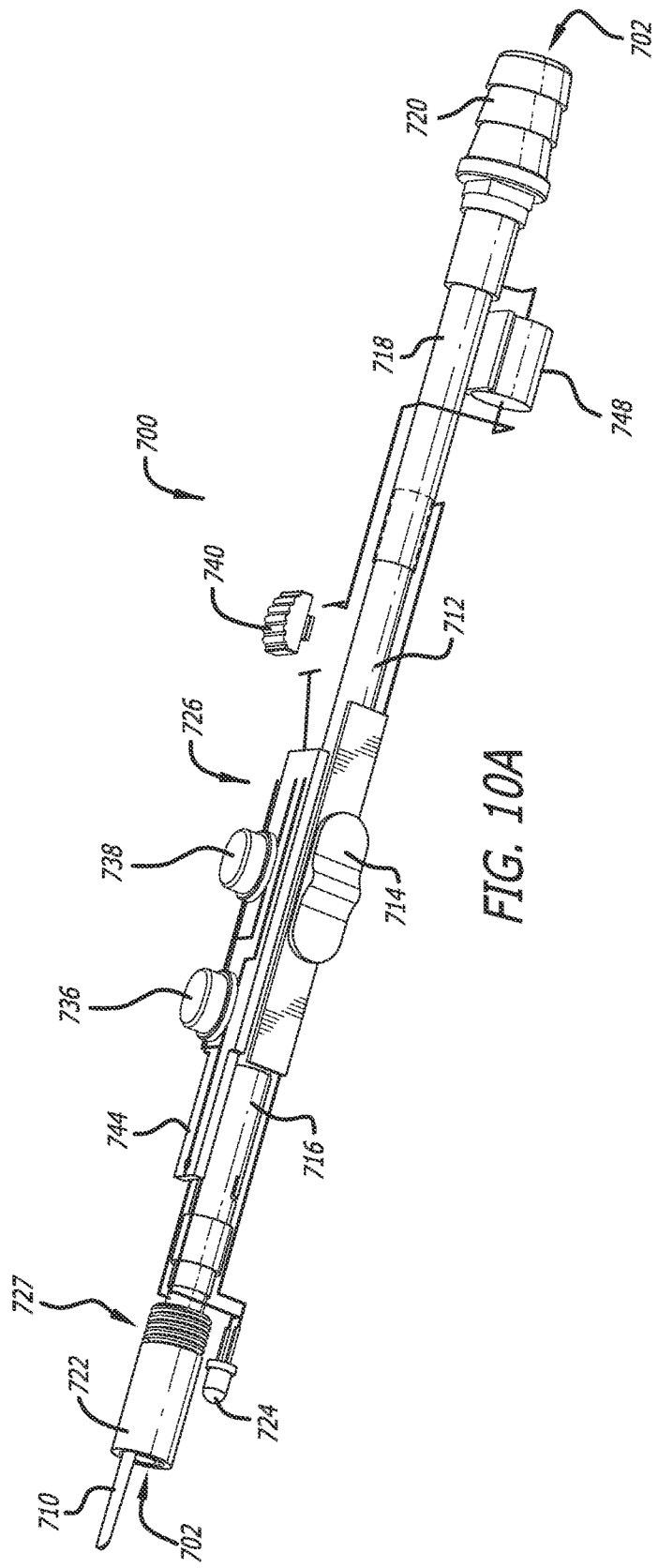
FIGS. 10A and 10B illustrate front, left side perspective view of the surgical pencil of FIG. 7, illustrating the cutting tool moving from the extended position to the retracted position.
Figure 10B:
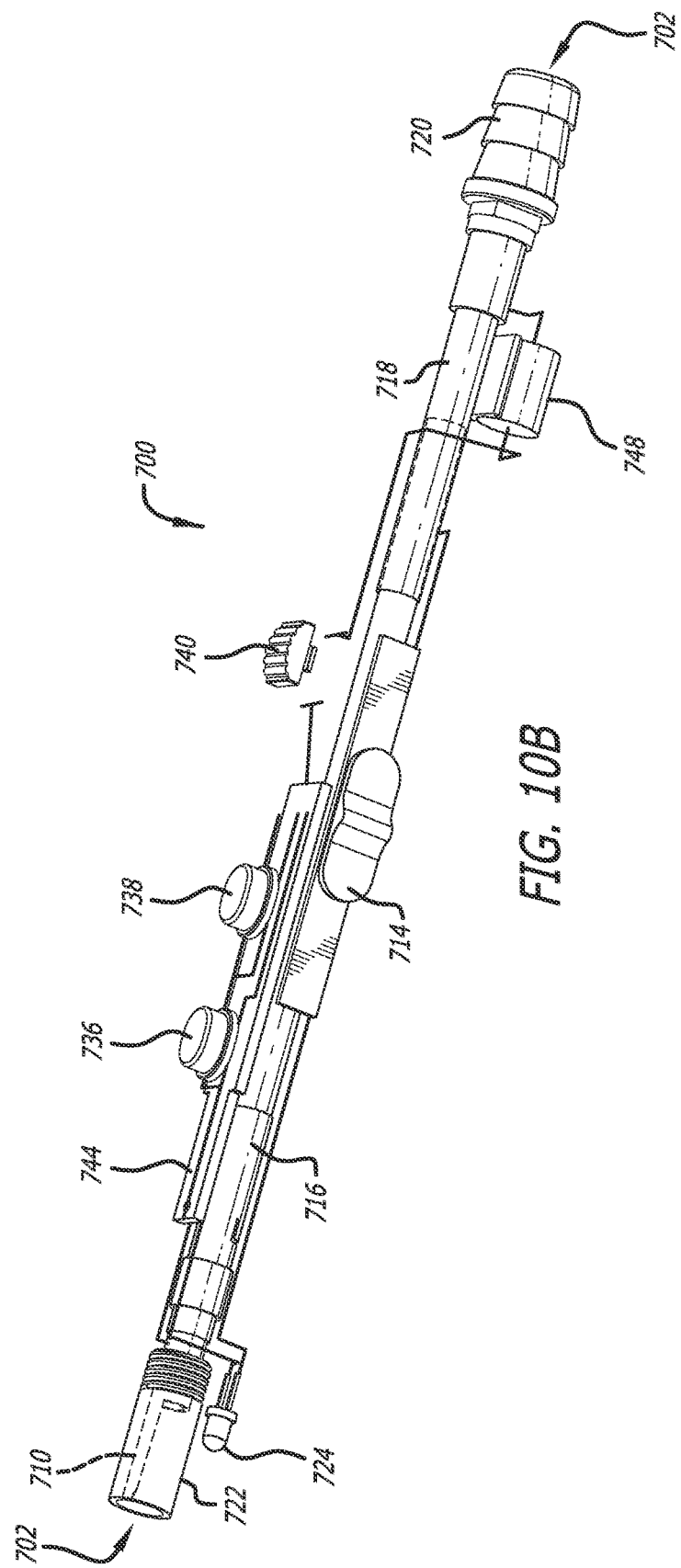
Figure 11:
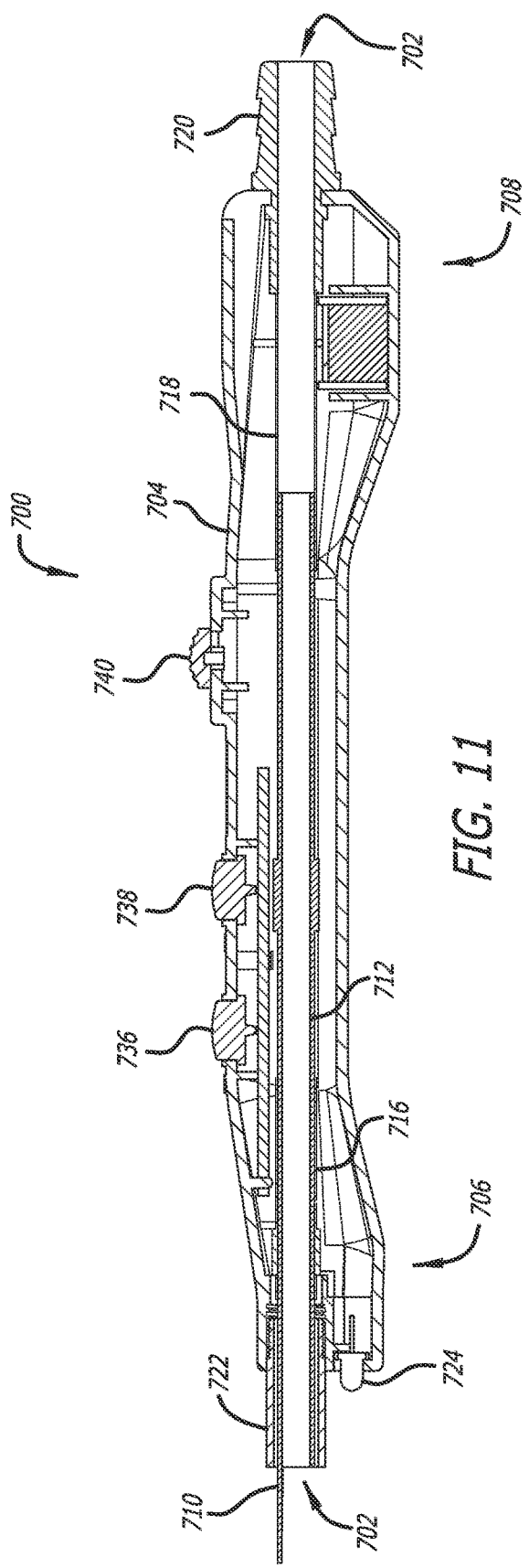
FIG. 11 illustrates a cross-sectional perspective view of the surgical pencil of FIG. 7, illustrating the cutting tool and the elongated tube being formed or made from the same material.

Referring now to FIGS. 7 to 11, in one example embodiment, surgical pencil 700 includes or defines a channel or pathway generally indicated at 702. As best illustrated in FIG. 11, in this example, channel 702 has a fairly consistent cross-section which runs from one end of surgical pencil 700 to the opposite end of surgical pencil 700. In this example, surgical pencil 700 includes a plurality of components (discussed in more detail below) which define the channel. It should be appreciated that in an alternative example, the channel or pathway can be defined by a single component such as a single tube, pipe or conduit. In one example embodiment, the housing of the surgical pencil defines the channel or passage 702.

Referring to FIGS. 7 to 12, in one example embodiment, surgical pencil 700 includes (a) housing 704 having (i) a first end portion generally indicated at 706; and (ii) a second end portion generally indicated at 708; (b) surgical tool 710; (c) elongated tube 712 connected to surgical tool 710; (d) slider 714 connected to the elongated tube 712; (e) first structure 716 positioned at the first end portion 706 and configured to receive and direct or support a portion of the elongated tube 712; (f) second structure 718 positioned at the second end portion and configured to receive and direct or support elongated tube 708; (g) connector 720 configured to connect to a separate discharge hose (not shown); (h) cylinder portion 722 removably connected to the housing; (i) lighting device generally indicated at 724; and (j) control system generally indicated at 726.

As illustrated in FIGS. 7 to 11, in one example embodiment, cylinder portion 722 is directly connected to housing 702. In this example embodiment, cylinder portion 722 is connected to housing 702 using a threaded connection. As illustrated in FIGS. 8 to 11, cylinder portion 722 includes threaded portion 727. In this example, threaded end portion 727 enables cylinder portion 722 to be removably connected to a threaded portion (not shown) of housing 702. It should be appreciated that the cylinder portion can connect to the housing using any suitable connection. In one example embodiment, the cylinder portion is permanently fixed to the housing. In one example embodiment, the cylinder portion is molded with the housing. That is, the cylinder portion and the housing form a single component of the surgical pencil.

As best illustrated in FIG. 10B, cylinder portion 722 is configured to house or enclose surgical tool 710 when surgical 710 is in the retracted state or position. It should be understood, that where the surgical pencil has a retracted position, during a surgical procedure, the user is enabled to position the end of the cylinder portion closer to the patient to provide for a more effective suction for materials such as blood. Furthermore, it should be apparent that the retracted state of the surgical pencil may prevent possible injuries caused by the exposure of the metal tip.

In one example embodiment, cylinder portion 722 forms a portion of the suction channel. For example, as illustrated in FIGS. 7 to 11, cylinder portion 722 forms part of the suction channel. In the example surgical pencil of FIGS. 7 to 12, the suction channel is formed by: (a) cylinder portion 722; (b) elongated tube 712; (c) second structure 718; and connector 720. As discussed above, it should be appreciated that the suction channel can be formed in any suitable way. For example, the channel may be formed by a single tube, pipe or conduit.

It should be appreciated that, in different embodiments, the cylinder portion can employ a different shape. The cylinder portion may be any suitable shape. For example, in one example embodiment, the cylinder portion can have a square cross-section.

In one example embodiment, because the cylinder portion is likely contact materials such as blood during a surgical procedure, the cylinder portion is configured to be removed and discarded after each use. Afterwards, a new cylinder portion may be connected to the housing for another surgical procedure.

Referring to FIGS. 7 to 11, in one example embodiment, connector 720 has a ribbed surface. In this example, the ribbed surface enables a discharge hose (not shown) to be connected quickly and easily to the surgical pencil using the connector 720. In one example embodiment, the discharge hose is connected to the surgical pencil 700 by pushing the discharge hose onto the connector 720. In this example, the ribbed surface ensures that the discharge hose is tight-fit after connection.

In one example embodiment, connector 722 is removably connected to the discharge hose using a threaded connection.

In one example embodiment, the discharge hose can be connected to a separate suction device which is configured to cause suctioning of the material. In another example, the surgical pencil includes the suction device. That is the suction device is integrated with the surgical pencil. In one example, where the suction device is integrated within the surgical pencil, the surgical pencil includes a chamber which collects the materials being suctioned during the surgical procedure. In one example embodiment, where the suction device is integrated within the surgical pencil, the surgical pencil does not include a connector which is configured to connect to the separate suction device.

In one example embodiment, the surgical pencil includes a control system. In one example embodiment, the control system may include at least one processor, at least one memory device operatively connected to the at least one processor, at least one input device operatively connected to the at least one processor, and at least one output device operatively connected to the at least one processor.

The at least one processor may be any suitable processor unit of a kind normally used in such devices. In one example embodiment, the control system includes one or more digital processors, such as a digital microprocessor or a microcontroller based platform. In one example embodiment, the control system includes one or more analog control units such as a suitable integrated circuit or one or more application-specific integrated circuits (ASIC's). In one example embodiment, the control system is in communication with, or operable to access or exchange signals with the at least one memory device. In this example, the memory device stores program code or instructions, executable by the processor(s), to control the surgical pencil. In one example embodiment, such memory device includes: (a) RAM (MRAM); (b) ferroelectric RAM (FeRAM); (c) read only memory (ROM); (d) flash memory; (e) EEPROM (electrically erasable programmable read only memory); or a suitable combination of such memory devices. It should be appreciated that any other suitable magnetic, optical, or semiconductor memory may operate in conjunction with, or as part of, the surgical pencil.

In one example embodiment, the output devices include at least one display device. In one example embodiment, the display device includes an LCD screen which is located on a front of the surgical pencil, and allows a user to interact with the control system. In one example embodiment, the display device includes an interface. Using the interface, the user may control the operation of the surgical pencil.

The surgical pencil may be configured to cause the display device to display at least one of, configuration screens, summary information, error indicators in the case of a malfunction, and/or battery power information.

Figure 12:
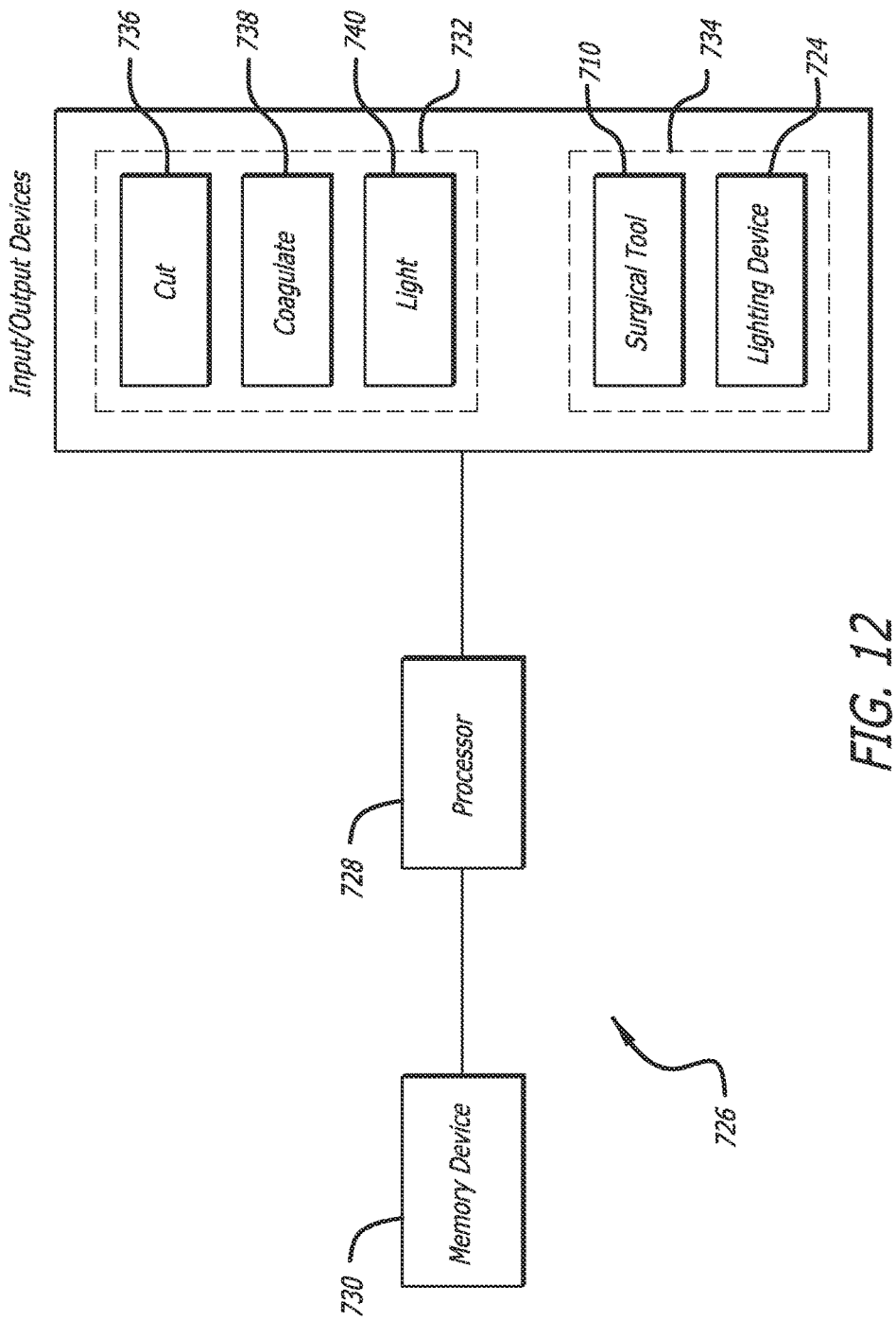
FIG. 12 illustrates a schematic diagram of the electronic configuration of the surgical pencil of FIG. 7, illustrating a processor, a memory device, input devices and output devices.

Referring to FIG. 12, control system 726 includes at least one processor 728; at least one memory device 730 operatively connected to processor 728; input devices 732 operatively coupled to processor 728; and output devices 734 operatively coupled to processor 728. In this example, as illustrated in FIGS. 7 to 12, input devices 732 include: (a) cut button 736; (b) coagulation button 738; and (c) light button 740. Output devices 1908 include: (a) surgical tool 710; and (b) light device 724. Control system 726 may be a portion of a control system for the surgical pencil (not shown).

Figure 8:
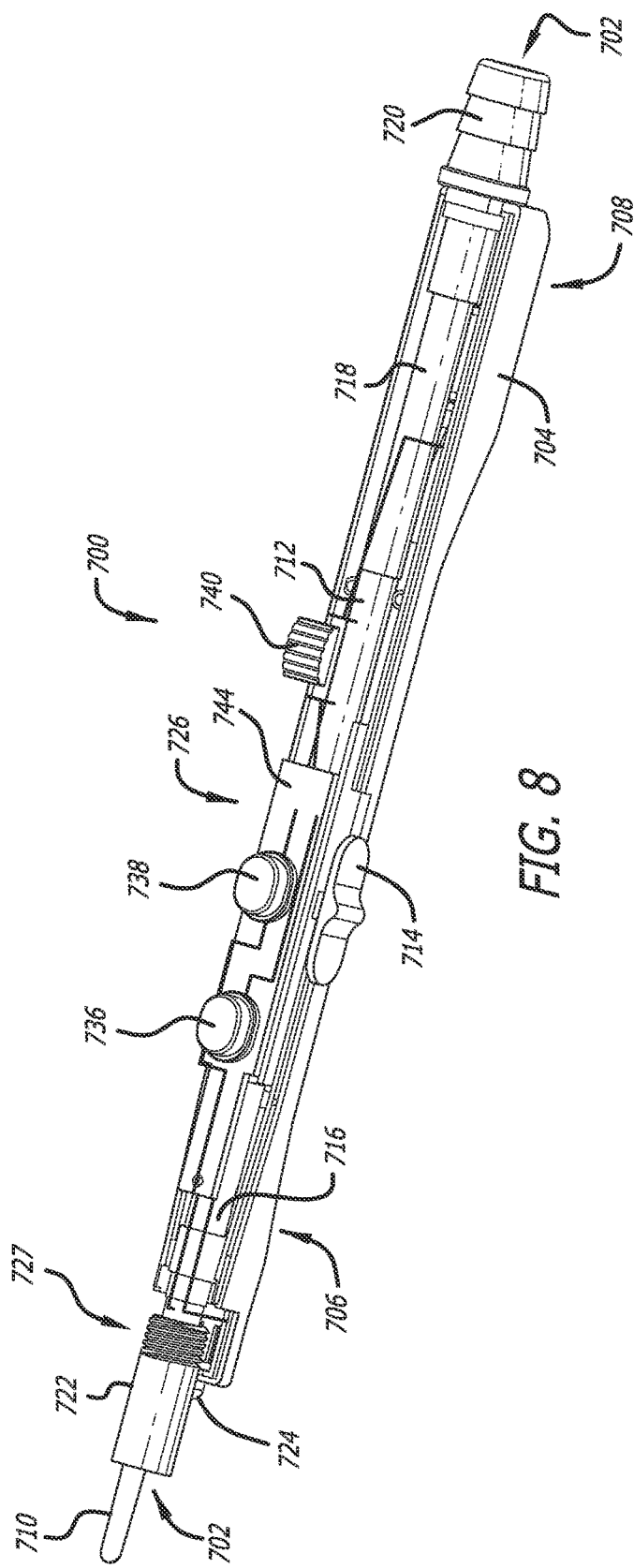
FIG. 8 illustrates top, left side perspective view of the surgical pencil of FIG. 7, illustrating the circuit board.

In one example embodiment, the surgical pencil includes a circuit board which includes the processor and memory device. For example, as best shown in FIGS. 8, 10A and 10B, the surgical pencil includes circuit board 744.

Figure 7:
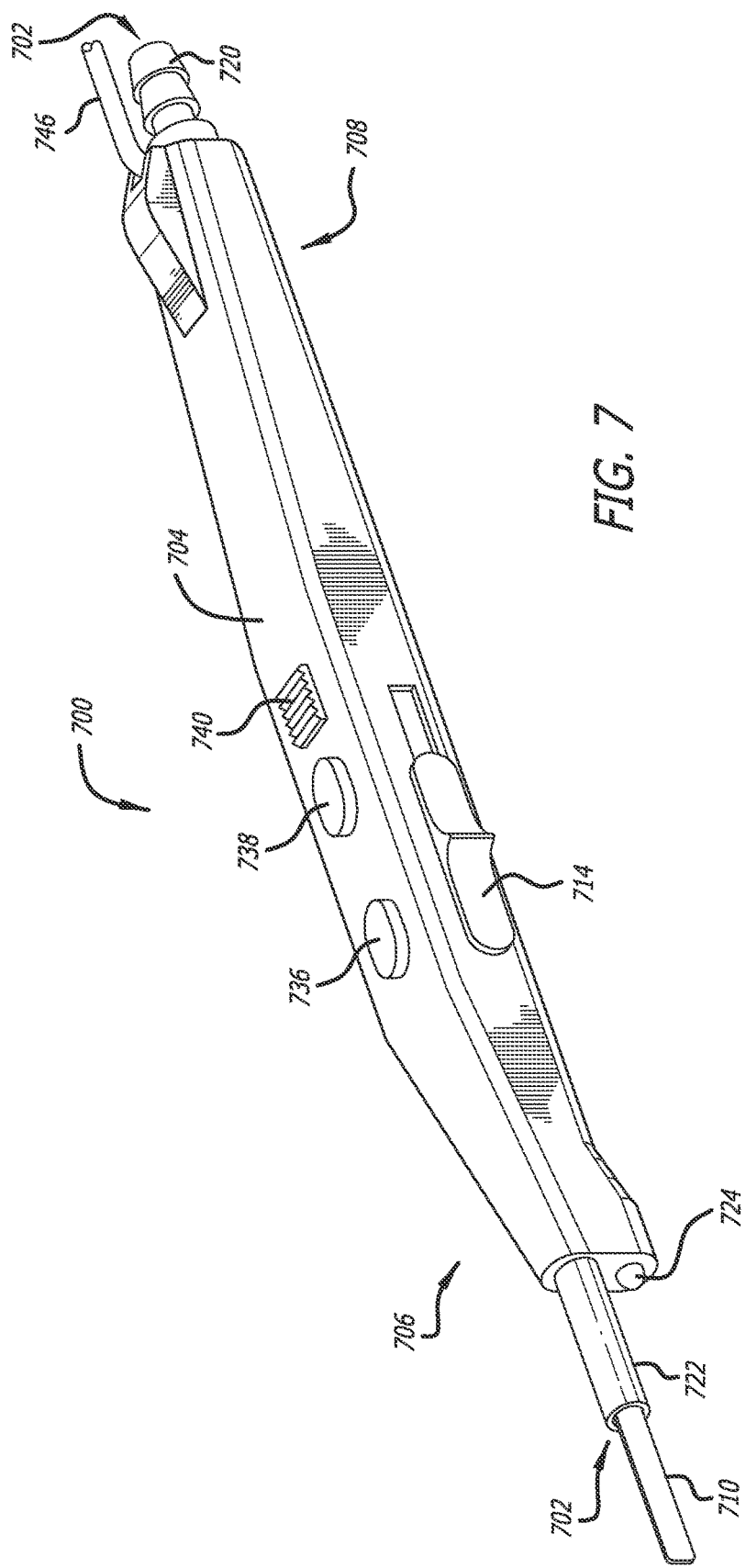
FIG. 7 illustrates a front, left side perspective view of one embodiment of the surgical pencil, illustrating the surgical tool being in an extended state.

In one example, the surgical pencil includes a cable or wire which supplies power to the control system. For example, as illustrated in FIG. 7, the surgical pencil includes cable 746. In one example embodiment, cable 746 provides at least two different electric currents with two different wave forms. In one example embodiment, an external power source such as an electrosurgical generator provides the two different currents with the two different wave forms. In one example embodiment, cable 746 provides electrical power to the lighting device. In another example, the surgical pencil includes a battery which is configured to provide power to the lighting device, For example, as illustrated in FIGS. 10A, 10B and 11, surgical pencil 700 includes battery 748 which provides power to light 742.

Figure 9:
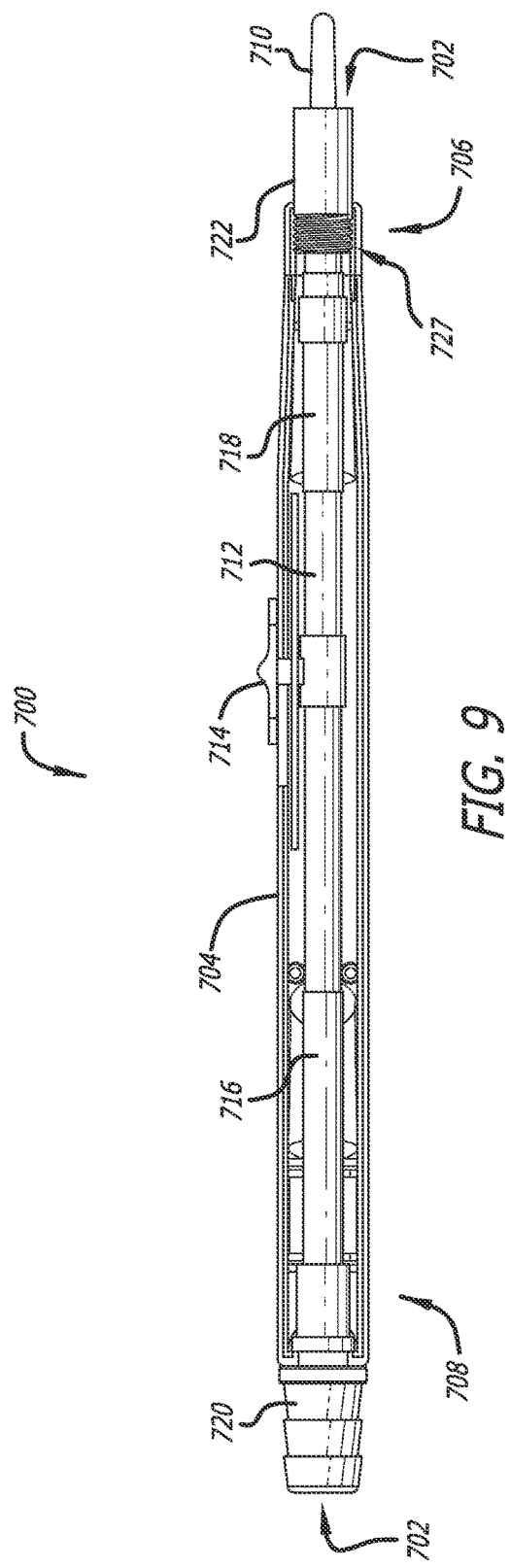
FIG. 9 illustrates a bottom perspective view of the surgical pencil of FIG. 7, illustrating the elongated tube being received by the first structure and the second structure.

Referring to the surgical pencil of FIGS. 7 to 12, in this example, surgical tool 710 is configured to move back and forth between: (a) an extended position (as illustrated in FIGS. 7 to 10A and 11); and (b) the retracted position (as illustrated in FIG. 10B). In this example, a user of surgical pencil 700 is enabled to control the position of cutting tool 710 using slider 714. More specifically, as best illustrated in FIG. 9, elongated tube 712 is connected to slider 714. First structure 716 and second structure 718 are configured to receive and direct elongated tube 712. Surgical tool 710 is connected to elongated tube 712. In response to slider 714 moving, elongated tube 712 is caused to matingly slide back and forth in first structure 716 and second structure 718. It follows that in response to elongated tube 712 moving back and forth, cutting tool 710 moves back and forth.

As illustrated in FIG. 10B, in this example, cutting tool 710 is in a retracted position. During a surgical procedure, a user is enabled to position the end of cylinder portion 722 closer to the patient to provide for a more effective suction for materials such as blood. Using this example surgical pencil, the need for a dedicated person at the surgical site to remove smoke and/or blood is eliminated.

Figure 13:
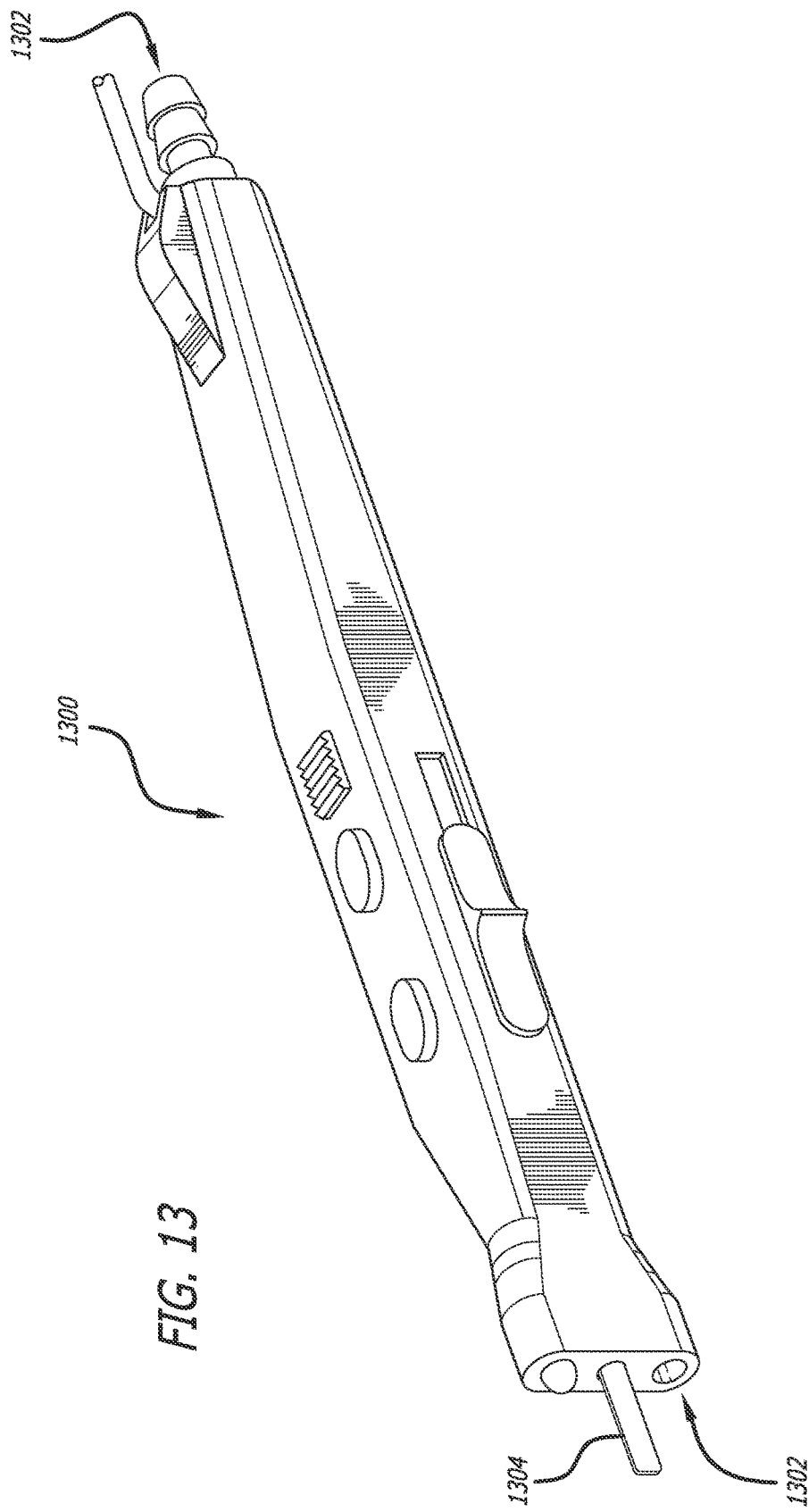
FIG. 13 illustrates a front, left side perspective view of one embodiment of the surgical pencil, illustrating the suction channel being positioned under the cutting tool.
Figure 14:
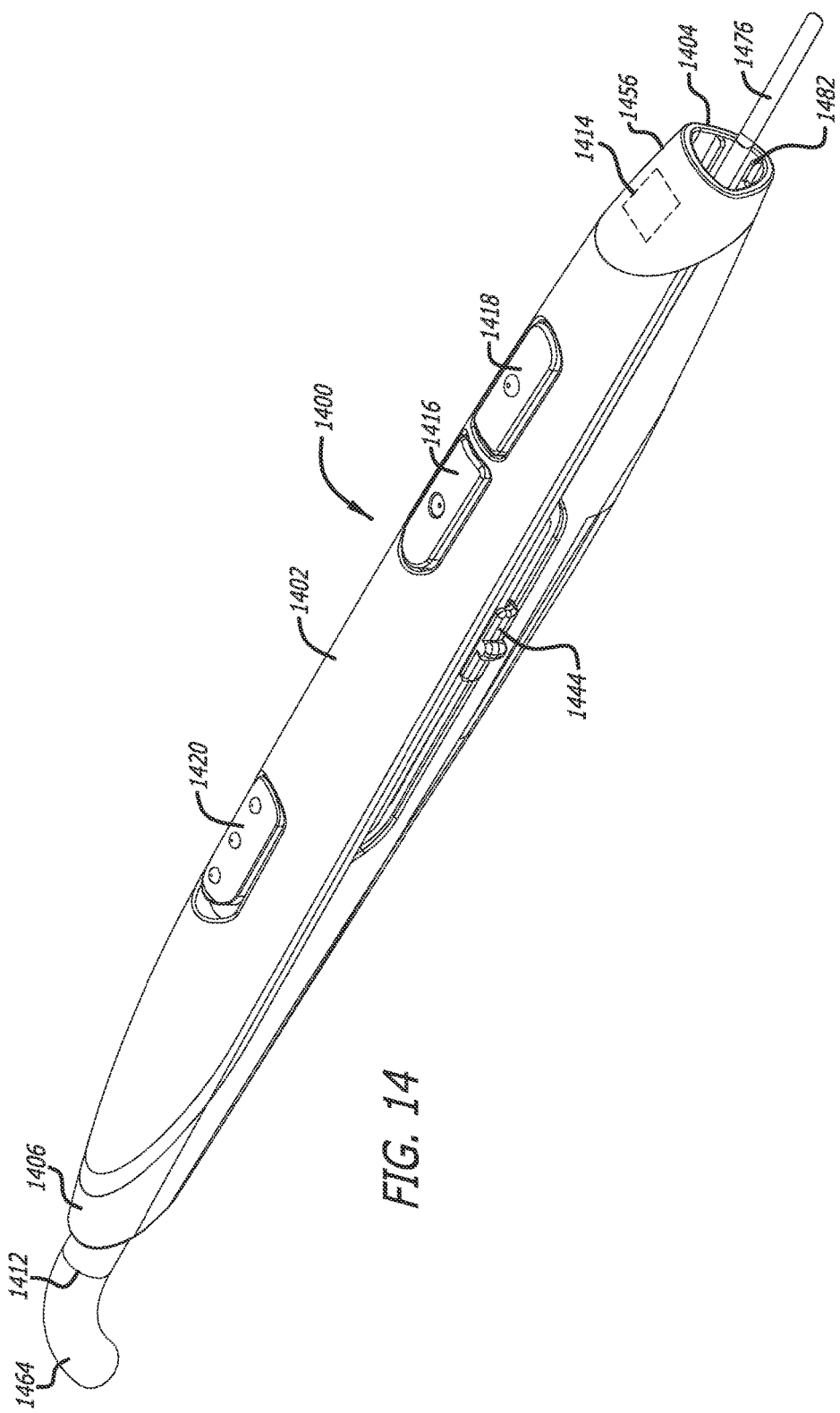
FIG. 14 illustrates another example embodiment of a surgical pencil in a perspective view with a surgical tool in an extended state.

In one example embodiment, components of the surgical pencil are arranged such that the formed suctioning channel is positioned bellow the cutting tool. For example, as illustrated in FIG. 13, surgical pencil 1300 includes or defines a channel or passage 1302 which enables suctioning and discharging of materials (e.g., smoke, blood, etc.). In this example, channel 1302 is positioned separate from and under cutting tool 1304.

In one example embodiment, where the surgical pencil enables suction, the surgical pencil may not include a lighting device. In other words, in some embodiments, a surgical pencil enabling suction may not have a lighting device associated with it.

In one example embodiment, surgical pencils can be configured to enable suctioning and discharging of materials through the surgical pencil's body cavity.

Referring now to FIGS. 14 to 23, in one example embodiment, surgical pencil 1400 includes housing 1402. Surgical pencil 1400 can also include a first end portion or proximal end 1404, a second end portion or distal end 1406, surgical tool 1408, slider 1410, discharge port 1412, and lighting device 1414. Surgical pencil can be controlled through coagulation button 1416 and cut button 1418. Lighting device 1414 can be controlled by light button 1420. Light button 1420 can be in the form of a push button, a rocker switch, a slider switch, a twist or dial switch, a touch sensitive switch, or the like. In one embodiment, light button 1420 is a slider switch.

In some embodiments, light button 1420 can control the intensity of light 1458. For example, light button 1420 can provide a gradient of light intensity. In one embodiment, light button 1420 is a slider switch with light intensity control.

Figure 18:
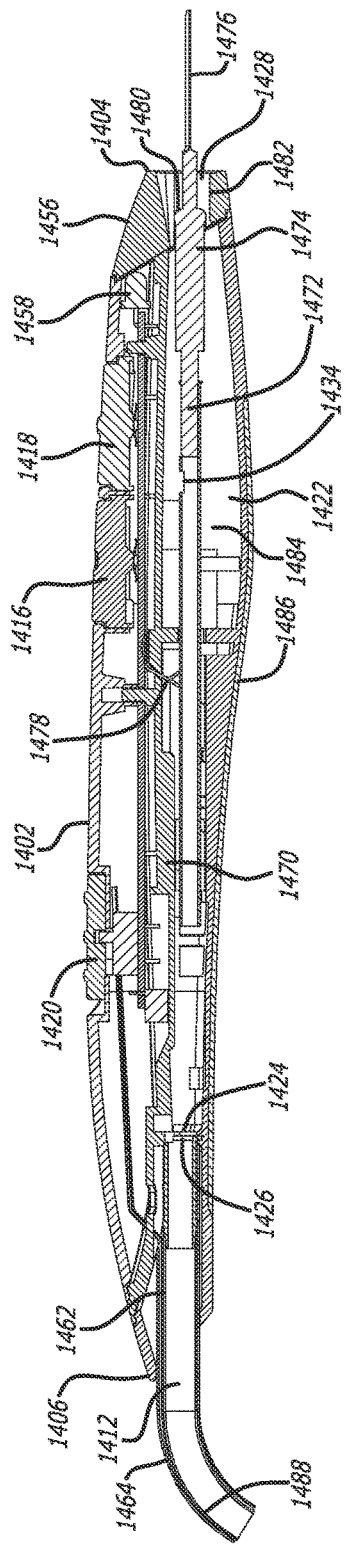
FIG. 18 illustrates a cross-sectional view of the surgical pencil in FIG. 14.
Figure 19:
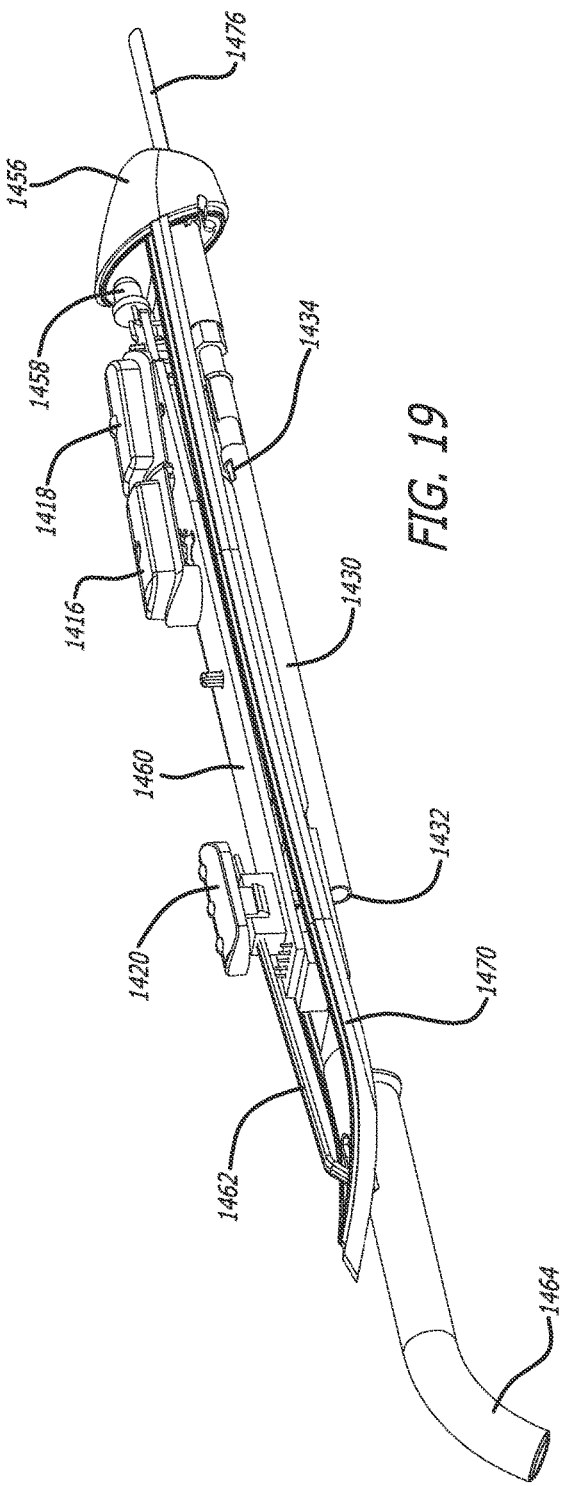
FIG. 19 illustrates a view of exemplary internal components of the surgical pencil in FIG. 14.
Figure 20:
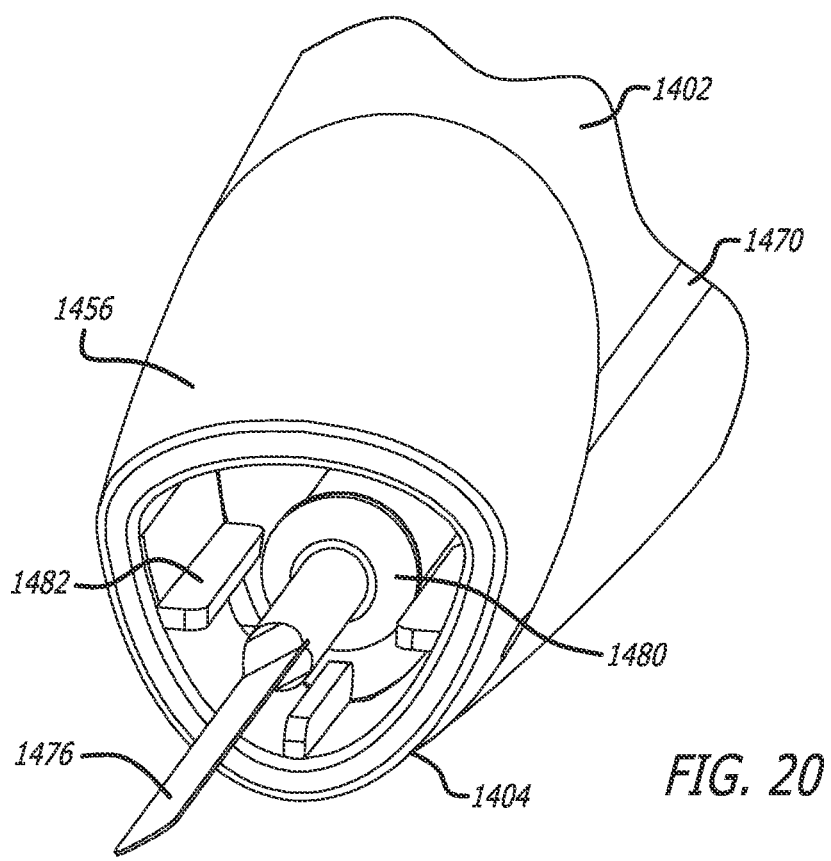
FIG. 20 illustrates a zoomed in view of the proximal end of the surgical pencil in FIG. 14 with the surgical tool extended.

Suction at or near proximal end 1404 can be provided by or configured to be provided by a channel or pathway through housing 1402 originating at discharge port 1412. As illustrated in FIG. 18, discharge port 1412 provides suction to interior chamber 1422 of housing 1402. Interior chamber is defined from distal point 1424 at the exit 1426 of discharge and electronics port 1412 to exit 1428 at proximal end 1404.

Suction can also be provided through elongated tube 1430 which is configured to connect to and receive surgical tool 1408. Suction can originate in elongated tube 1430 through origin port 1432 and can be delivered to entry port 1434.

In some embodiments, surgical tool 1408 (or 710) can be user replaceable. In other embodiments, surgical tool 1408 (or 710) can be permanently welded, glued or otherwise attached to elongated tube 1430. Surgical tools can be fitted into coupling mechanism 1436 which can be any mechanism that holds surgical tool in place during a procedure and allows the correct current to run through the tool. In some embodiments, coupling mechanism 1436 can be a friction fit. In other embodiments, coupling mechanism 1436 can be a threaded coupling.

Elongated tube 1430 can be coupled to or otherwise extend through slider 1410. Slider 1410 can include ring portion 1440 through which elongated tube 1430 can be threaded. Ring portion 1440 can assist in supporting elongated tube 1430; in particular, ring portion 1440 can support the distal portion of elongated tube. In some embodiments, ring portion need not be a complete ring. For example, ring portion 1440 can be a half ring in some embodiments. Slider portion can also include nesting portion 1442 that support a center portion of elongated tube 1430. Nesting portion 1442 can be in a half circle configuration. In other embodiments, nesting portion 1442 can be a complete ring or substantially a complete ring.

Slider 1410 can further include finger actuators 1444 that can be engaged by one or more fingers to extend or retract surgical tools. Finger actuators 1444 can be configured to engage with tracks 1446 that include peaks 1448 and valleys 1450. Finger actuators 1444 can include a protrusion (not shown) that can nest in a valley and lock slider 1410 between two peaks. In other embodiments, a protrusion 1490 can be situated in slider 1410 that can lock in a valley 1450 between two peaks 1448. Lockability of slider 1410 can be beneficial to surgeons in that locking slider in particular positions can prevent involuntary extending or retracting surgical tools.

Tracks 1446 can provide lockable positions about every 0.5 cm, 1 cm, 1.5 cm, 2 cm, between about 0.5 cm and about 2 cm, between about 1 cm and about 2 cm, or at least about 0.5 cm.

In some embodiments, a slider is not used to adjust the position (e.g., retracted or extended) of a surgical tool. Some embodiments use a wheel to dial a desired extended or retracted position for a surgical tool. Such a wheel can be calibrated for different length surgical tools.

The wheel can be linked to or include a sprocket that engages a track that can move (e.g., extend or retract) the elongated tube 1430 and hence a surgical tool attached thereto.

In some embodiments, using a slider including finger actuators to extend and retract a surgical tool may prevent possible injuries caused by the exposure to the metal tip. Further, the use of a slider including finger actuators to extend and retract a surgical tool can prevent a user from having to grasp a surgical tool or a suction tube directly. A slider including finger actuators allows a surgeon or other user to extend and retract a surgical tool without risk of injuring him/herself and without interrupting the surgery to manually grasp and move the surgical tool. For example, without a slider including finger actuators, in order to move a surgical tool or suction tubing, in order to prevent injury, the surgery must be put on hold, the surgical pencil unplugged, the tool or suction tube moved, the surgical pencil plugged in and the surgery commenced. This is complicated, time consuming and dangerous. Time can be saved while a patient is under anesthetic using the presently described devices because the surgery need not be stopped or substantially delayed in order to extend or retract a surgical tool or suction tube.

Housing 1402 can further include support members 1452 positioned at or near proximal end 1404. Support members 1452 can be configured to receive and direct or support a portion of elongated tube 1430. In some embodiments, support members can support proximal portion of elongated tube 1430. Further, distal support members 1454 can be configured to receive and direct or support a distal portion of elongated tube 1430. In other embodiments, housing 1402 can include three, four, five, six, seven, eight, nine, ten or more sets of support members. For example, in one embodiment, housing 1402 can include support members 1452 which can be considered proximal support members, distal support members 1454, and one or more sets of support members in between, such as middle support members.

Proximal end 1404 of housing 1402 can include a transparent or partially transparent portion 1456. Transparency of at least a portion of transparent or partially transparent portion 1456 can allow light 1458 to shine there though. Light 1458 can be any light as described herein.

Surgical pencil 1400 can further include a control system as described herein. Control system can be at least partially configured to run off of or from printed circuit board 1460. Printed circuit board 1460 can include at least one processor as described herein. Printed circuit board 1460 can be sealed in an airtight compartment or in a compartment separate from suctioning. In some embodiments, printed circuit board 1460 is configured to be water or liquid proof. In some embodiments, printed circuit board 1460 can be coated with a material that prevents damage to the board when subjected to water, solvents, blood, or other body tissue.

Power can be supplied to printed circuit board 1460 by wire bundle 1462. Wire bundle 1462 can be housed within an inner lumen of suction tubing 1464. Wire bundle 1462 can be housed within the wall of suction tubing 1464. Wire bundle 1462 can be housed within a second tube adjacent to or connected to suction tubing 1464. Wire bundle can also be housed in a space between suction tubing 1464 and a second larger tube 1488; or in other words, sandwiched in between the outer surface of suction tubing 1464 and the inner surface of second larger tube 1488.

In one example embodiment, suction tubing 1464 can be connected to a separate suction device which is configured to cause suctioning of the material. In another example, the surgical pencil includes the suction device. That is the suction device can be integrated with the surgical pencil. In one example, where the suction device is integrated within the surgical pencil, the surgical pencil includes a chamber which collects the materials being suctioned during the surgical procedure. In one example embodiment, where the suction device is integrated within the surgical pencil, the surgical pencil does not include a connector which is configured to connect to the separate suction device.

Figure 21:
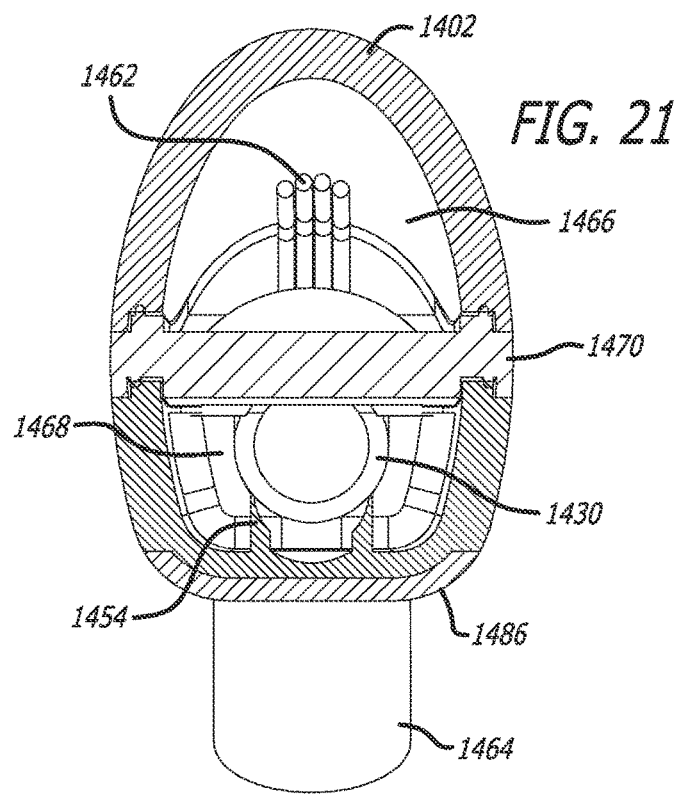
FIG. 21 illustrates another cross-sectional view of the surgical pencil in FIG.
Figure 22:
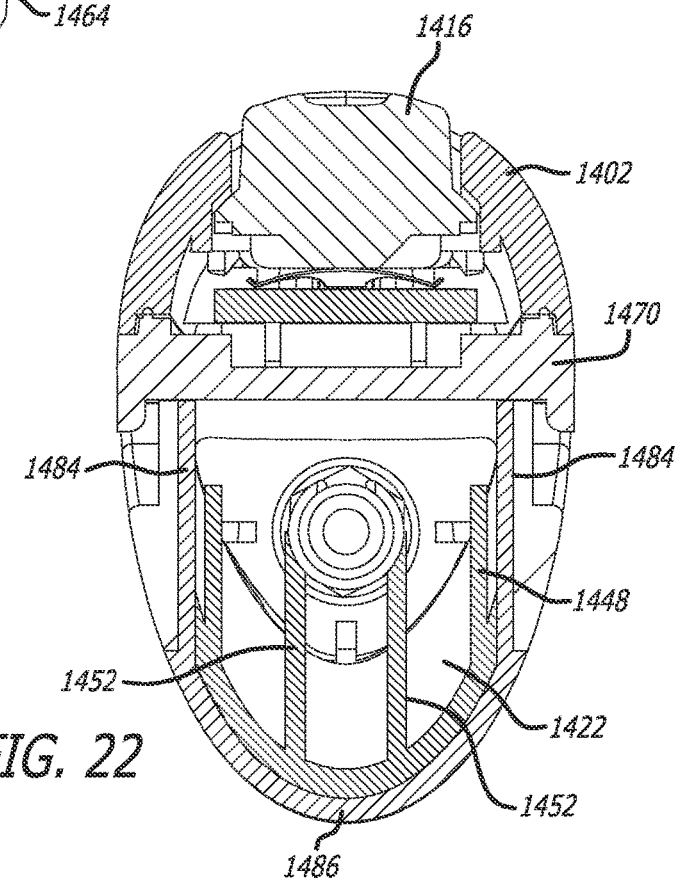
FIG. 22 illustrates another cross-sectional view of the surgical pencil in FIG.
Figure 23:
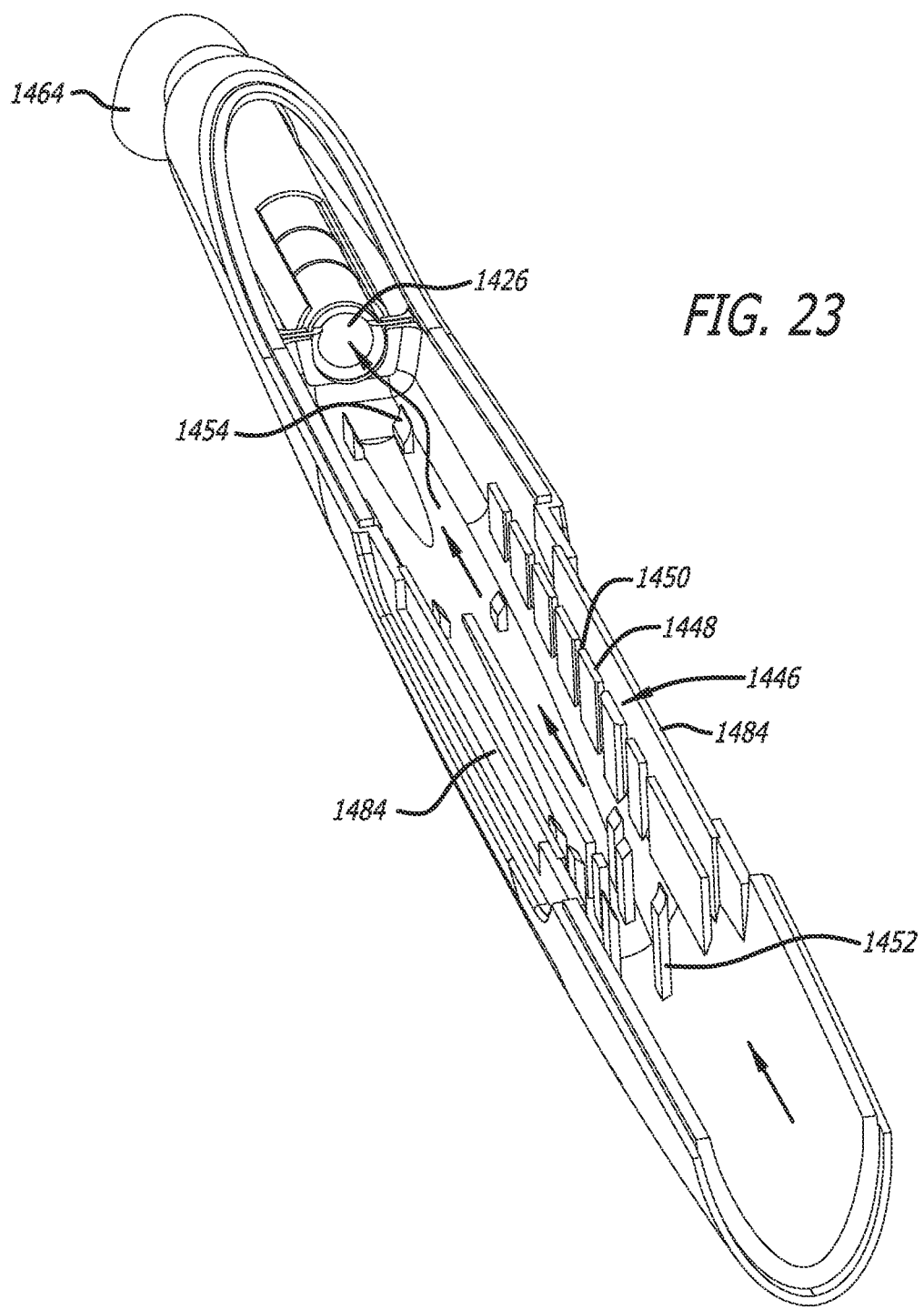
FIG. 23 illustrates example internal components of the surgical pencil in FIG. 14

In some embodiments, as illustrated in FIG. 21, housing 1402 can be split into an upper chamber 1466 and lower chamber 1468. In some embodiments, lower chamber 1468 can be configured to partake in suctioning activity and contact fluids, blood, and tissues. Upper chamber 1466 can be configured to be sealed off from lower chamber 1468 thereby preventing ingress of fluids, blood, and tissues. In some embodiments, printed circuit board can be housed in upper chamber 1466 thereby sealing it from lower chamber 1468. Separator 1470 can be used to at least partially divide upper chamber 1466 and lower chamber 1468. In some embodiments, the underside of printed circuit board can at least partially form the seal between upper chamber 1466 and lower chamber 1468.

Figure 15:
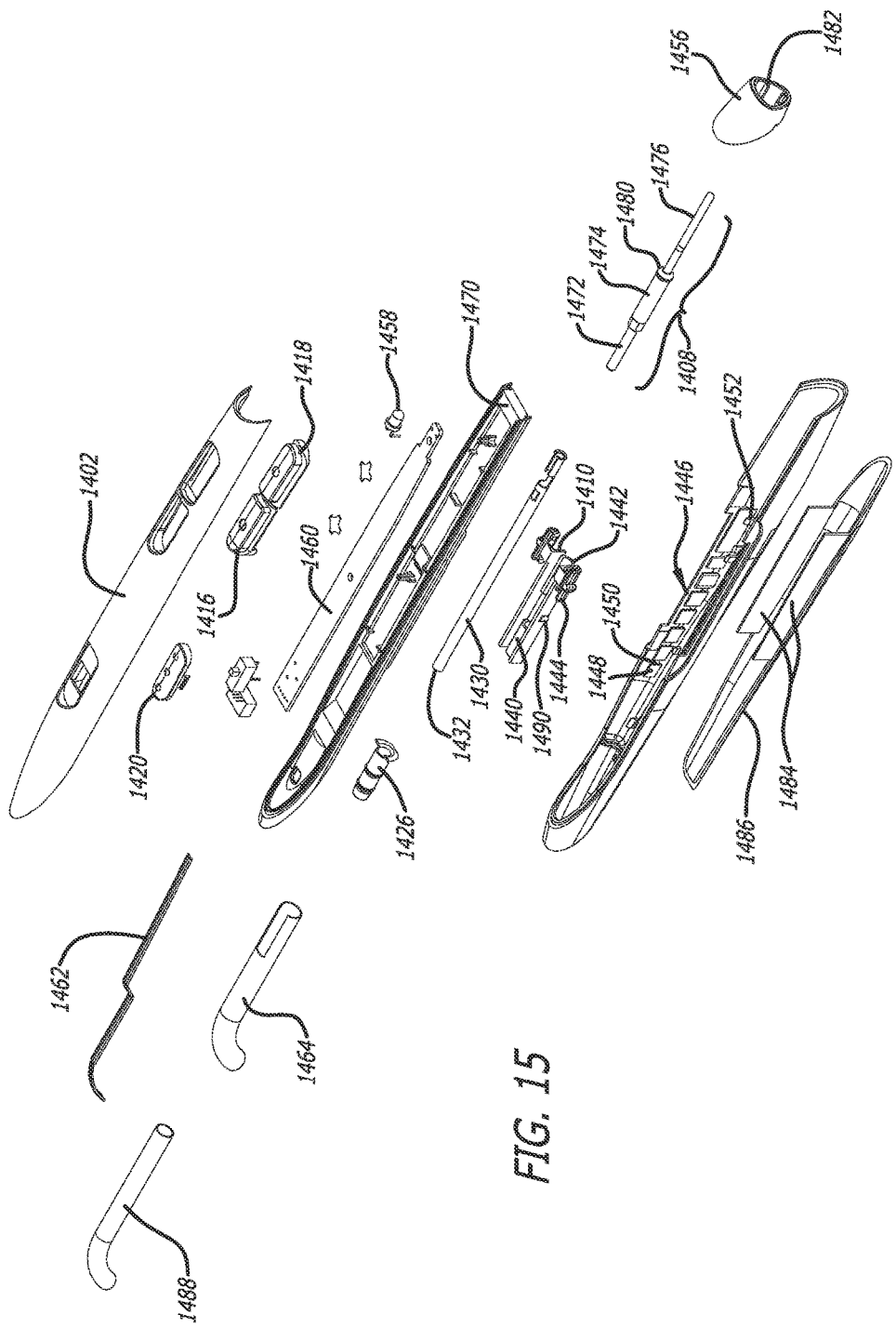
FIG. 15 illustrates an exploded view of the surgical pencil in FIG. 14.

In some embodiments, when surgical tool 1608 is removable from surgical pencil 1400, surgical tool 1408, as illustrated in FIG. 15, can include interface portion 1472, insulation portion 1474, and a tip 1476. Interface portion 1472 can be configured to engage or wed with coupling mechanism 1436. Further, interface portion 1472 can be formed of a conductive metal that can conduct electrical energy from elongated tube 1430. In some embodiments, elongated tube 1430 is also formed of a conductive metal that can accept electrical current from printed circuit board 1460 via conducting wire 1478. Conducting wire can physically engage elongated tube 1430 even when elongated tube 1430 is being moved axially to extend and retract surgical tool 1408.

In other embodiments, elongated tube 1430 may not be formed of a conductive metal but includes a channel of conductive metal such as a strip that can accept electrical current from printed circuit board 1460 via conducting wire 1478. Conducting wire can physically engage a conductive metal strip along elongated tube 1430 even when elongated tube 1430 is being moved axially to extend and retract surgical tool 1408.

Tip 1476 can be formed completely or substantially of a metal as described herein. Further, tips described herein, e.g., tip 1476, can have shapes as required for particular medical procedures. For example, tips can be flat or substantially flat. In other embodiments, tips can be cylindrical. Tips can have blunt ends or sharp ends.

In some embodiments, tips as used herein do not include forcept tips, clamps, or the like. In some embodiments, tips include configurations that can cut while passing along a tissue rather than cutting tissues by clamping or shearing the tissues using scissors or scissor-like devices. Tips as described herein may not be used to clamp a tissue between two tips and then cut/cauterize the clamped tissues. Rather, tips described can freely cut tissues without the need of clamping.

Insulation portion 1474 can be formed of a non-metallic or non-conducting material. However, in some embodiments, insulation portion 1474 can be formed of a metal and coated or covered by a non-metallic or non-conducting material. Insulation portion 1474 can be formed such that when it touches housing 1402, any current running through the surgical pencil is not transmitted to the housing. Further, insulation portion 1474 can include a lip 1480 to enable a user to grip and remove surgical tool 1408 from surgical pencil 1400. In some embodiments, lip 1480 is not included on insulation portion 1474.

Exit 1428 at proximal end 1404 can include one or more guides 1482. Guides assist in insertion of surgical tool 1408 into coupling mechanism 1436 by aligning interface portion 1472 with coupling mechanism 1436. Further, when tip 1476 is extended from exit 1428, one or more guides 1482 can assist in supporting insulation portion 1474.

In some embodiments, surgical pencils described herein can include a cylinder portion or tube that surrounds a surgical tool. This tube can be extended or retracted from the housing to provide an extended suction tube beyond the surgical tool. In some embodiments, a surgical tool may be locked in place or created as a stationary tool and an extendable suction tube can provide suction beyond the tool. For example, a user may have a surgical tool locked in a favorite extended position. T circumferential tube can be extended beyond the surgical tool to provide suction as needed without using the surgical tool. A slider can be used to extend and retract the suction tube as required. The retracted state of the surgical tool may prevent possible injuries caused by the exposure to the metal tip.

Any suction tube described herein can include one or more vacuum relief holes to prevent damages to tissues from clogging the vacuum line.

Retractability of surgical tools or tips as described herein can be useful to a surgeon or other user because at portions of surgery, simply suctioning smoke, fluids, blood, or tissues may be desired without the use of the tip or tool. As such, when not needed, the tip or tool can be retracted into the housing and not interfere with suctioning or that portion of the surgery.

Retractability supplied by a slider can be supplemented by a barrier such as barrier member 1484. Barrier member 1484 can be configured to assist in presenting loss of suction at or near a surgical tool. Barrier member can be formed of a malleable polymer that can deform as portions of slider 1410 pass by. In other embodiments, brushes or bristles can be used in place of a polymer.

Barrier member 1484 can also serve as a vacuum relief. If exit 1428 at proximal end 1404 becomes obstructed during operation, vacuum pressure can be relived through holes created between barrier member 1484 folding down where slider 1410 is located. Therefore, with barrier member 1484, exit 1428 may not be able to damage tissue with vacuum pressure.

Barrier member can optionally be integrated onto grip portion 1486. Grip portion 1486 can form a portion of the bottom of surgical pencil 1400. Grip portion can assist with gripping the surgical pencil during use.

On the other hand, the tip or tool can be extended for use to cut and/or cauterize. In any case, suction around the tip is not interrupted. Suction can occur circumferentially around the tip and/or the surgical tool. In some embodiments, even when the surgical tool is being extended or retracted, suction is not interrupted. Further still, the tip can be completely or substantially retracted into the body of the surgical pencil or tool to allow the device to be used as a standalone suction device. The retractability of the tip can be effectuated using a slider or slider mechanism as described herein.

In some embodiments, the surgical tools described herein are not endoscopic tools and may not be configured to tunnel through a catheter or completely within a tissue or tissues. Rather, the surgical pencils described herein can be designed to use in the hand of a user in a manner similar to a pen, pencil, or stylus.

The surgical pencils described herein including or enabling suctioning can be configured to deliver a vacuum pressure or suction pressure of about 10 mm-Hg, about 20 mm-Hg, about 30 mm-Hg, about 40 mm-Hg, about 50 mm-Hg, about 60 mm-Hg, about 70 mm-Hg, about 80 mm-Hg, about 90 mm-Hg, about 100 mm-Hg, about 140 mm-Hg, about 180 mm-Hg, about 200 mm-Hg, about 240 mm-Hg, about 280 mm-Hg, about 300 mm-Hg, about 340 mm-Hg, about 380 mm-Hg, about 400 mm-Hg, about 440 mm-Hg, about 480 mm-Hg, about 500 mm-Hg, between about 10 mm-Hg and about 500 mm-Hg, between about 50 mm-Hg and about 480 mm-Hg, between about 100 mm-Hg and about 500 mm-Hg, at least about 10 mm-Hg, at least about 30 mm-Hg, at least about 50 mm-Hg, at least about 80 mm-Hg, or at least about 100 mm-Hg. In some embodiments, this can be continuous surgical suction.

Unless otherwise indicated, all numbers expressing quantities of ingredients, properties such as molecular weight, reaction conditions, and so forth used in the specification and claims are to be understood as being modified in all instances by the term "about." Accordingly, unless indicated to the contrary, the numerical parameters set forth in the specification and attached claims are approximations that may vary depending upon the desired properties sought to be obtained by the present invention. At the very least, and not as an attempt to limit the application of the doctrine of equivalents to the scope of the claims, each numerical parameter should at least be construed in light of the number of reported significant digits and by applying ordinary rounding techniques. Notwithstanding that the numerical ranges and parameters setting forth the broad scope of the invention are approximations, the numerical values set forth in the specific examples are reported as precisely as possible. Any numerical value, however, inherently contains certain errors necessarily resulting from the standard deviation found in their respective testing measurements.

The terms "a," "an," "the" and similar referents used in the context of describing the invention (especially in the context of the following claims) are to be construed to cover both the singular and the plural, unless otherwise indicated herein or clearly contradicted by context. Recitation of ranges of values herein is merely intended to serve as a shorthand method of referring individually to each separate value falling within the range. Unless otherwise indicated herein, each individual value is incorporated into the specification as if it were individually recited herein. All methods described herein can be performed in any suitable order unless otherwise indicated herein or otherwise clearly contradicted by context. The use of any and all examples, or exemplary language (e.g., "such as") provided herein is intended merely to better illuminate the invention and does not pose a limitation on the scope of the invention otherwise claimed. No language in the specification should be construed as indicating any non-claimed element essential to the practice of the invention.

Groupings of alternative elements or embodiments of the invention disclosed herein are not to be construed as limitations. Each group member may be referred to and claimed individually or in any combination with other members of the group or other elements found herein. It is anticipated that one or more members of a group may be included in, or deleted from, a group for reasons of convenience and/or patentability. When any such inclusion or deletion occurs, the specification is deemed to contain the group as modified thus fulfilling the written description of all Markush groups used in the appended claims.

Certain embodiments of this invention are described herein, including the best mode known to the inventors for carrying out the invention. Of course, variations on these described embodiments will become apparent to those of ordinary skill in the art upon reading the foregoing description. The inventor expects skilled artisans to employ such variations as appropriate, and the inventors intend for the invention to be practiced otherwise than specifically described herein. Accordingly, this invention includes all modifications and equivalents of the subject matter recited in the claims appended hereto as permitted by applicable law. Moreover, any combination of the above-described elements in all possible variations thereof is encompassed by the invention unless otherwise indicated herein or otherwise clearly contradicted by context.

Specific example embodiments disclosed herein may be further limited in the claims using consisting of or and consisting essentially of language. When used in the claims, whether as filed or added per amendment, the transition term "consisting of" excludes any element, step, or ingredient not specified in the claims. The transition term "consisting essentially of" limits the scope of a claim to the specified materials or steps and those that do not materially affect the basic and novel characteristic(s). Example embodiments of the invention so claimed are inherently or expressly described and enabled herein.

In closing, it is to be understood that the embodiments of the invention disclosed herein are illustrative of the principles of the present invention. Other modifications that may be employed are within the scope of the invention. Thus, by way of example, but not of limitation, alternative configurations of the present invention may be utilized in accordance with the teachings herein. Accordingly, the present invention is not limited to that precisely as shown and described.

The invention is claimed as follows:

1. A surgical pencil comprising:
   a housing, and
   a surgical tool including a tip configured to perform one of cutting and coagulation, wherein the housing includes a channel terminating near the tip and allowing suctioning at a surgery site, wherein the tip is attachable to an elongated tube including an actuator, and wherein the tip is moveable from an extended position to a retracted position completely within the channel without disturbing suctioning by moving the actuator between lockable positions in valleys on a track including peaks and valleys.

2. The surgical pencil of claim 1, wherein the tip is formed substantially of a metal.

3. The surgical pencil of claim 1, further including a light.

4. The surgical pencil of claim 1, wherein the surgical tool is replaceable.

5. The surgical pencil of claim 1, wherein suctioning is provided circumferentially around the surgical tool.

6. The surgical pencil of claim 1, further comprising a printed circuit board configured to control the surgical pencil.

7. The surgical pencil of claim 6, wherein the elongated tube is configured to couple the surgical tool to the printed circuit board.

8. The surgical pencil of claim 7, wherein the elongated tube is configured to couple the surgical tool to the printed circuit board when moving the surgical tool.

9. The surgical pencil of claim 7, wherein the elongated tube is configured to allow suctioning through a lumen running axially through the elongated tube.

10. The surgical pencil of claim 1 providing a suctioning of between about 50 mm-Hg and about 480 mm-Hg.

* * * * *